United States Patent
Zergiebel et al.

(10) Patent No.: US 9,801,646 B2
(45) Date of Patent: Oct. 31, 2017

(54) ADAPTER LOAD BUTTON DECOUPLED FROM LOADING UNIT SENSOR

(71) Applicant: Covidien LP, Mansfield, MA (US)

(72) Inventors: Earl M. Zergiebel, Guilford, CT (US); Russell Pribanic, Roxbury, CT (US); David Chowaniec, Rocky Hill, CT (US); Ryan V. Williams, Milford, CT (US); Jonathan W. Sapienza, Orange, CT (US)

(73) Assignee: Covidien LP, Mansfield, MA (US)

( * ) Notice: Subject to any disclaimer, the term of this patent is extended or adjusted under 35 U.S.C. 154(b) by 647 days.

(21) Appl. No.: 14/274,173

(22) Filed: May 9, 2014

(65) Prior Publication Data

US 2014/0358129 A1  Dec. 4, 2014

Related U.S. Application Data

(60) Provisional application No. 61/828,726, filed on May 30, 2013.

(51) Int. Cl.
*A61B 17/00* (2006.01)
*A61B 17/32* (2006.01)
(Continued)

(52) U.S. Cl.
CPC ........... *A61B 17/320016* (2013.01); *A61B 17/07207* (2013.01); *A61B 17/28* (2013.01);
(Continued)

(58) Field of Classification Search
CPC ...... A61B 17/320016; A61B 17/07207; A61B 17/28; A61B 2017/0046;
(Continued)

(56) References Cited

U.S. PATENT DOCUMENTS 2,777,340 A  1/1957  Hettwer et al.
2,957,353 A  10/1960  Babacz
(Continued)

FOREIGN PATENT DOCUMENTS

AU  2008229795 A1  4/2009
CA  2451558 A1  1/2003
(Continued)

OTHER PUBLICATIONS

European Search Report No. 14170464.3 dated Feb. 23, 2015, 9 pages.
(Continued)

*Primary Examiner* — Michael Carey

(57) ABSTRACT

A surgical device is provided. The surgical device includes: a jaw assembly comprising a first jaw and a second jaw moveable relative to the first jaw and an elongated body removably coupled to a proximal end of the jaw assembly. The elongated body includes an actuation bar movable upon engagement of the jaw assembly with the elongated body to secure the jaw assembly thereto; a release button coupled to the actuation bar such that the release button is movable by the actuation bar upon engagement of the jaw assembly with the elongated body and the release button is configured to move the actuation bar to allow for removal of the jaw assembly from the elongated body; and a lockout button in mechanical cooperation with the release button, the lockout button configured to prevent actuation of the release button.

17 Claims, 30 Drawing Sheets

(51) Int. Cl.
*A61B 17/28* (2006.01)
*A61B 17/072* (2006.01)
*A61B 17/29* (2006.01)
*A61B 90/00* (2016.01)

(52) U.S. Cl.
CPC .......... *A61B 2017/0046* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/2808* (2013.01); *A61B 2017/2946* (2013.01); *A61B 2090/0808* (2016.02)

(58) Field of Classification Search
CPC  A61B 2017/00398; A61B 2017/00464; A61B 2017/00473; A61B 2017/00477; A61B 2017/00734; A61B 2017/2808; A61B 2017/2946
USPC .............. 606/1, 39, 45, 46, 51, 52
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |

(56) References Cited

U.S. PATENT DOCUMENTS

| | | |
|---|---|---|
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |

(56) References Cited

U.S. PATENT DOCUMENTS

| | | |
|---|---|---|
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0179374 A1* | 7/2008 | Beardsley ........ A61B 17/07207 227/176.1 |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0057078 A1 | 3/2010 | Arts et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |

(56) References Cited

FOREIGN PATENT DOCUMENTS

| | | |
|---|---|---|
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 00/72760 A1 | 12/2000 |
| WO | 00/72765 A1 | 12/2000 |
| WO | 03/000138 A1 | 1/2003 |
| WO | 03/026511 A1 | 4/2003 |
| WO | 03/030743 A2 | 4/2003 |
| WO | 03065916 A1 | 8/2003 |
| WO | 03/077769 A1 | 9/2003 |
| WO | 03090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, mailed Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
International Search Report corresponding to PCT/US2005/027266, completed May 30, 2008 and mailed Jun. 18, 2008; (2 pp.).
Extended European Search Report corresponding to EP 08 25 2703.7, completed Oct. 23, 2008 and mailed Oct. 31, 2008; (7 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.

(56) References Cited

OTHER PUBLICATIONS

Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to Application No. EP 14152236.7 mailed May 12, 2014.
Chinese Office Action dated Aug. 18, 2017 issued in corresponding Chinese Patent Application No. 2014102403740.

* cited by examiner

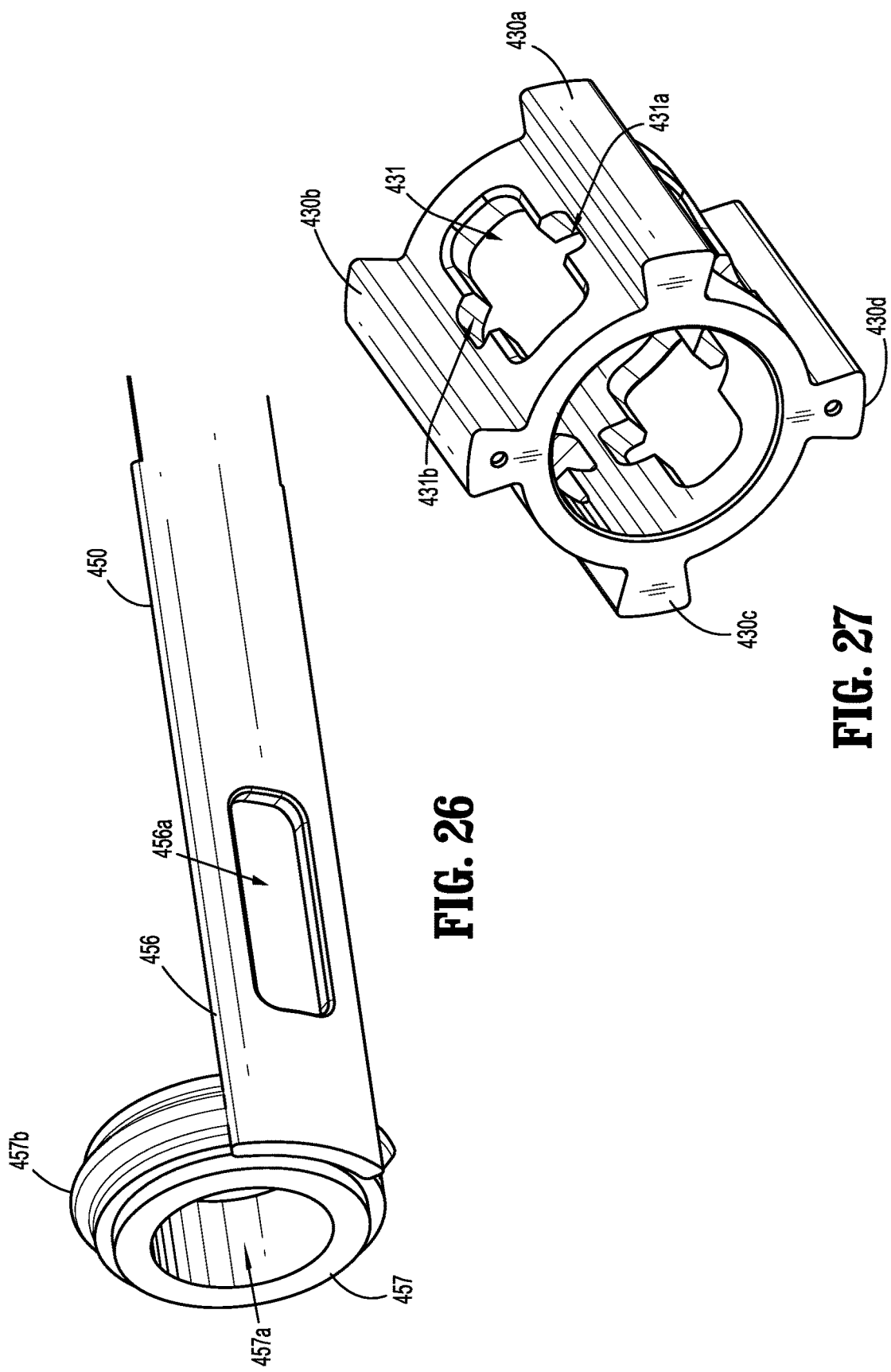

ADAPTER LOAD BUTTON DECOUPLED FROM LOADING UNIT SENSOR

CROSS-REFERENCE TO RELATED APPLICATIONS

This application claims the benefit of and priority to U.S. Provisional Patent Application No. 61/828,726, filed May 30, 2013, the entire disclosure of which is incorporated by reference herein.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatuses, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a reusable handle assembly, and disposable or single use loading units. The loading units are selectively connected to the handle assembly prior to use and then disconnected from the handle assembly following use in order to be disposed of or in some instances sterilized for re-use.

Many of the existing end effectors for use with many of the existing surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven surgical devices and/or handle assemblies that include locking and release mechanisms for coupling to the end effectors.

SUMMARY

Further details and aspects of exemplary embodiments of the present invention are described in more detail below with reference to the appended Figures.

According to an embodiment of the present disclosure, a surgical device adapter for coupling an end effector to a handle assembly is disclosed. The surgical device adapter includes: a sensor link assembly engagable by the end effector upon coupling the end effector to the surgical device adapter; a load link movable by the end effector from a first position to a second position, wherein in the second position the load link locks the sensor link assembly and in the first position releases the sensor link assembly; and a sensor engagable by the sensor link assembly upon proximal movement thereof in response to release by the load link.

According to another aspect of the present disclosure, the load link is distally biased and is configured to prevent proximal movement of the sensor link assembly until the load link is distally biased and the end effector is coupled to the surgical device adapter.

According to another aspect of the present disclosure, the surgical device adapter further includes a lock spring actuatable by proximal movement of the load link, the lock spring configured to couple to a proximal portion of the sensor link assembly and prevent proximal movement thereof.

According to another aspect of the present disclosure, the sensor link assembly includes a proximal sensor link, a distal sensor link and a biasing member disposed therebetween.

According to another aspect of the present disclosure, the proximal sensor link includes a ring configured to interface with the lock spring.

According to another aspect of the present disclosure, the adapter includes a bayonet connection at a distal end thereof configured to couple to a pair of lugs of the end effector.

According to another aspect of the present disclosure, the end effector is configured to be inserted linearly into the bayonet connection.

According to another aspect of the present disclosure, load link is moved proximally to allow for rotation of lugs within the bayonet connection.

According to another aspect of the present disclosure, at least one lug of the pair of lugs engages the distal sensor link upon rotation of the end effector within the bayonet connection thereby compressing the biasing member.

According to another aspect of the present disclosure, the load link is moved distally to secure at least one lug of the pair of lugs within the bayonet connection.

According to another aspect of the present disclosure, distal movement of the load link releases the lock spring allowing the biasing member to move the proximal sensor link proximally to engage the sensor.

According to another embodiment of the present disclosure, a method an end effector to a surgical device adapter. The method includes the steps of: inserting an end effector including a pair of lugs disposed at a proximal end thereof into a distal end of the surgical device adapter; proximally moving a distally-biased load link within the surgical device adapter to secure a sensor link assembly; rotating the end effector within the adapter assembly, wherein at least one lug of the pair of lugs engages and secured at least a portion of the sensor link assembly; and distally moving the load link to secure the end effector within the surgical device adapter and to release the sensor link assembly allowing the sensor link assembly to move proximally to engage a sensor.

According to another aspect of the present disclosure, the sensor link assembly includes a distally-biased proximal sensor link, a distal sensor link, and a biasing member disposed therebetween.

According to another aspect of the present disclosure, moving the load link proximally secures the proximal sensor link.

According to another aspect of the present disclosure, rotating the end effector engages at least one lug of the pair of lugs engages the distal sensor link thereby compressing the biasing member.

According to another aspect of the present disclosure, moving the load link distally secures at least one lug of the pair of lugs to release the proximal sensor link allowing the biasing member to move the proximal sensor link proximally to engage the sensor.

According to another aspect of the present disclosure, the load link is coupled to the sensor link assembly via a biasing member at proximal ends thereof.

BRIEF DESCRIPTION OF THE DRAWINGS

Embodiments of the present disclosure are described herein with reference to the accompanying drawings, wherein:

FIG. 26 is a perspective view of a proximal portion of the proximal sensor link of FIG. 25, according to the present disclosure;

FIG. 27 is a perspective view of a seal spacer of the adapter assembly of FIG. 1, according to the present disclosure;

DETAILED DESCRIPTION OF EMBODIMENTS

Figure 1:
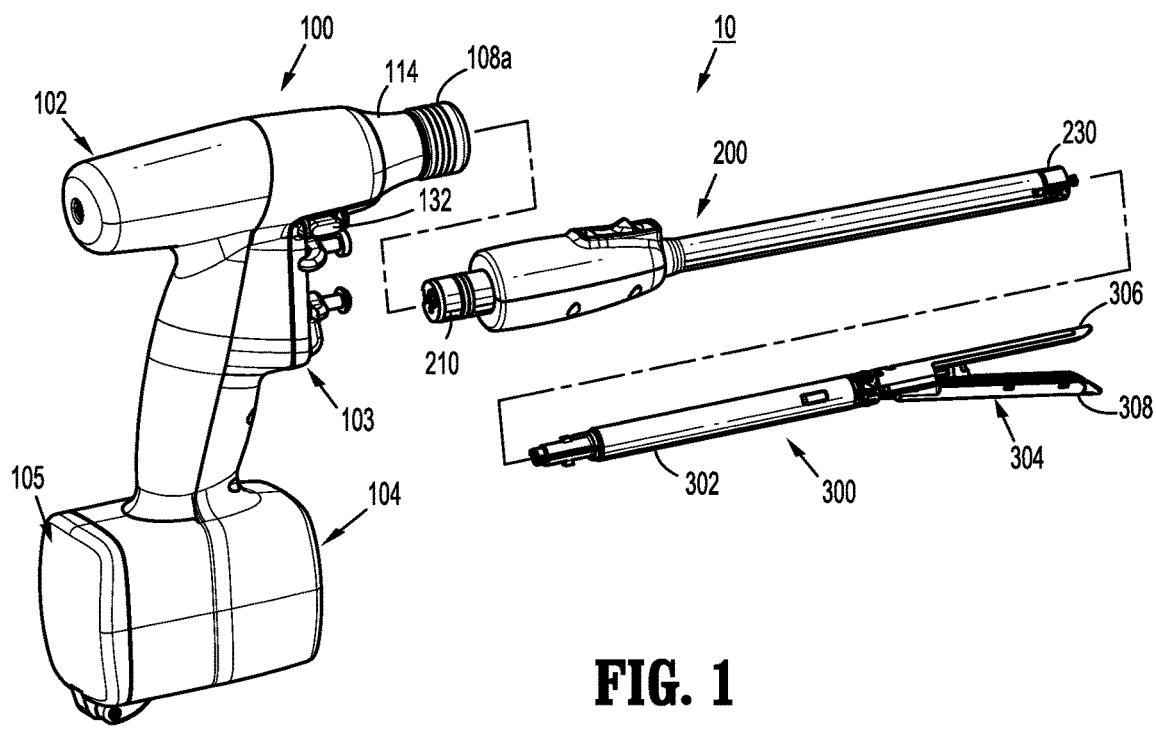
FIG. 1 is a perspective, disassembled view of an electromechanical surgical system including a surgical instrument, an adapter assembly, and an end effector, according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left and right sides, respectively, from the perspective of the user facing the distal end of the electromechanical surgical system, apparatus and/or device from the proximal end while the surgical system, apparatus and/or device is oriented in non-rotational configuration.

Referring initially to FIGS. 1-8, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 300, via an adapter assembly 200 (e.g., elongated body). The end effector 300 and the adapter assembly 200 are configured for actuation and manipulation by the electromechanical, hand-held, powered surgical instrument 100. In particular, the surgical instrument 100, the adapter assembly 200, and the end effector 300 are separable from each other such that the surgical instrument 100 is configured for selective connection with adapter assembly 200, and, in turn, adapter assembly 200 is configured for selective connection with any one of a plurality of different end effectors 300.

Reference may be made to U.S. Pat. No. 7,963,433, filed Sep. 22, 2008 and U.S. Patent Application Publication No. 2011/0121049, filed on Nov. 20, 2009, the entire contents of all of which are incorporated herein by reference, for a detailed description of the construction and operation of exemplary electromechanical, hand-held, powered surgical instrument 100.

Figure 2:
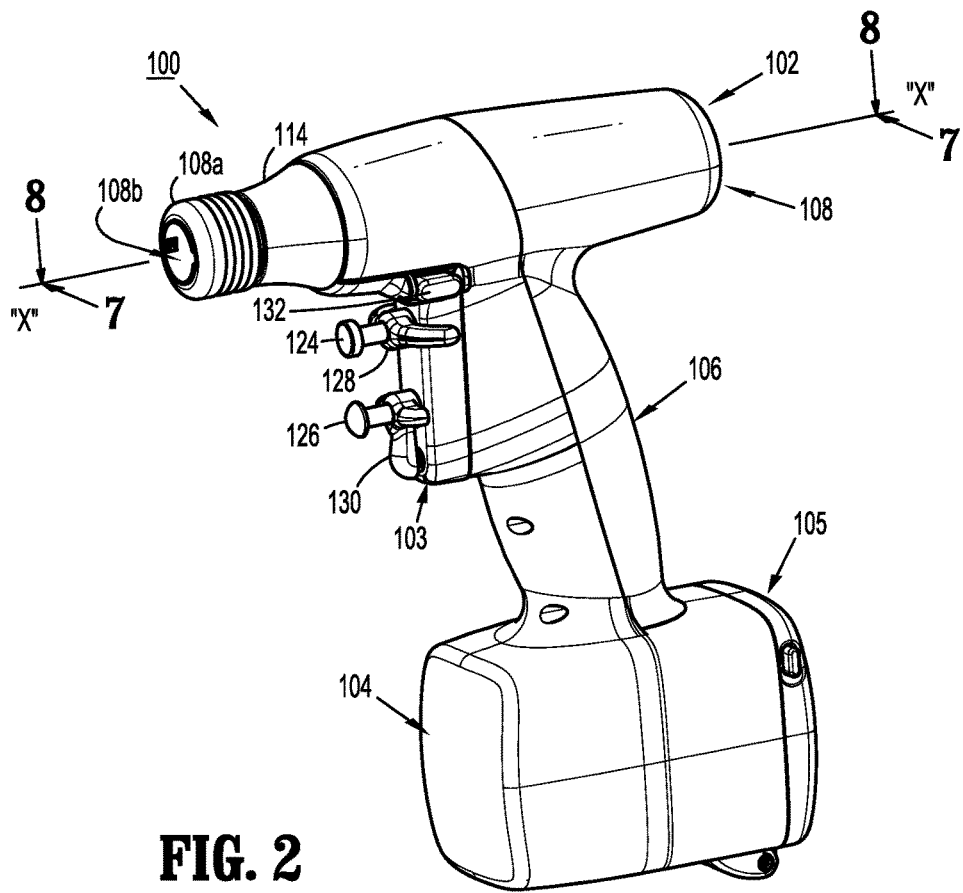
FIG. 2 is a perspective view of the surgical instrument of FIG. 1, according to the present disclosure.
Figure 3:
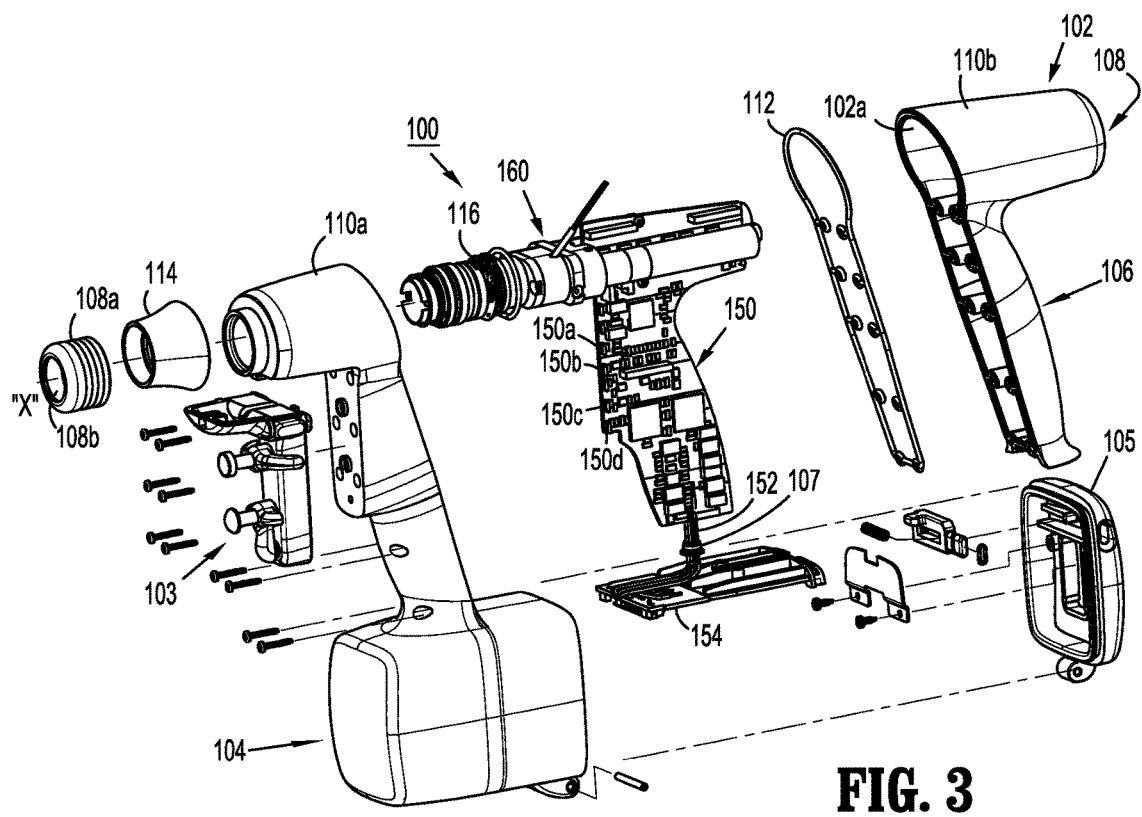
FIG. 3 is perspective, exploded view of the surgical instrument of FIG. 1, according to the present disclosure.

As illustrated in FIGS. 1-3, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

With reference to FIGS. 2 and 3, distal and proximal half-sections 110a, 110b are divided along a vertical plane that traverses a longitudinal axis "X-X" of upper housing portion 108. Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Figure 4:
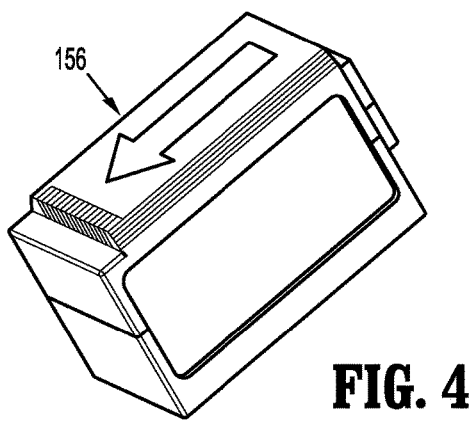
FIG. 4 is a perspective view of a battery of the surgical instrument of FIG. 1, according to the present disclosure.

Lower housing portion 104 of surgical instrument 100 defines an aperture (not shown) formed in an upper surface thereof and which is located beneath or within intermediate housing portion 106. As shown in FIGS. 3 and 4, the aperture of lower housing portion 104 provides a passage through which wires 152 pass to electrically interconnect electrical components situated in lower housing portion 104, e.g., a battery 156 and a circuit board 154, with electrical components situated in intermediate housing portion 106 and/or upper housing portion 108, e.g., circuit board 150, drive mechanism 160, etc.

Handle housing 102 includes a gasket 107 disposed within the aperture of lower housing portion 104 (not shown) thereby plugging or sealing the aperture of lower housing portion 104 while allowing wires 152 to pass therethrough. Gasket 107 functions to establish an air-tight seal between lower housing portion 106 and intermediate housing portion 108 such that circuit board 150 and drive mechanism 160 are protected from sterilization and/or cleaning procedures.

With continued reference to FIGS. 3 and 4, lower housing portion 104 of handle housing 102 provides a housing in which the battery 156 is removably disposed therein. The battery 156 may be a rechargeable battery (e.g., lead-based, nickel-based, lithium-ion based, etc.). It is also envisioned that the battery 156 may be a single-use, non-rechargeable battery. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

Figure 5:
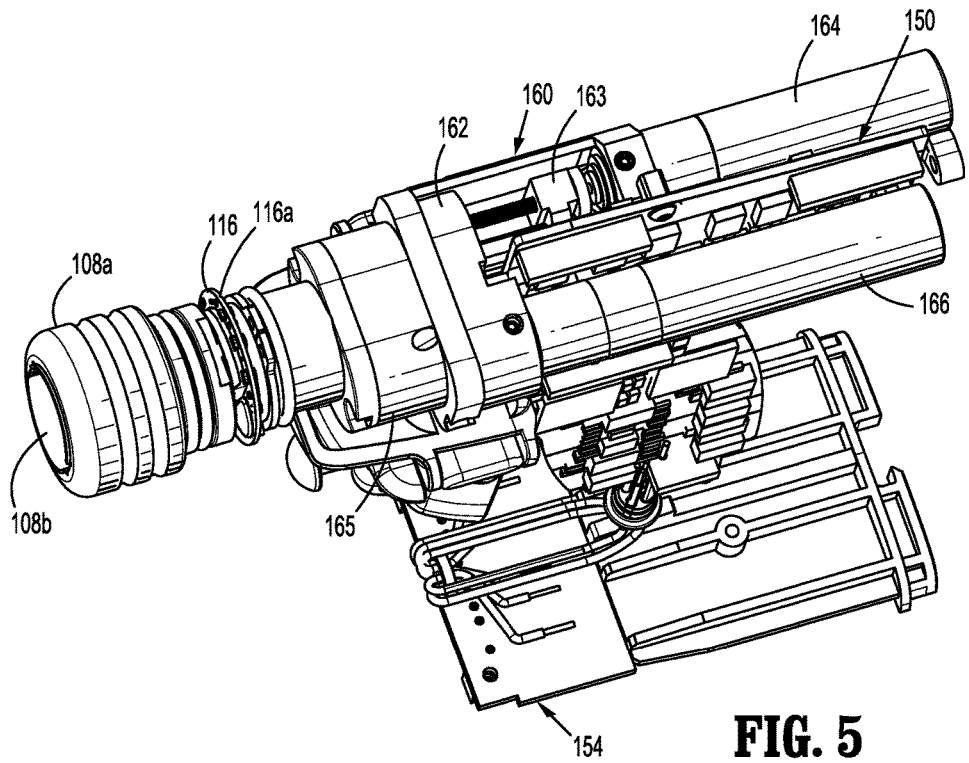
FIG. 5 is a top, partially-disassembled view of the surgical instrument of FIG. 1, according to the present disclosure.
Figure 6:
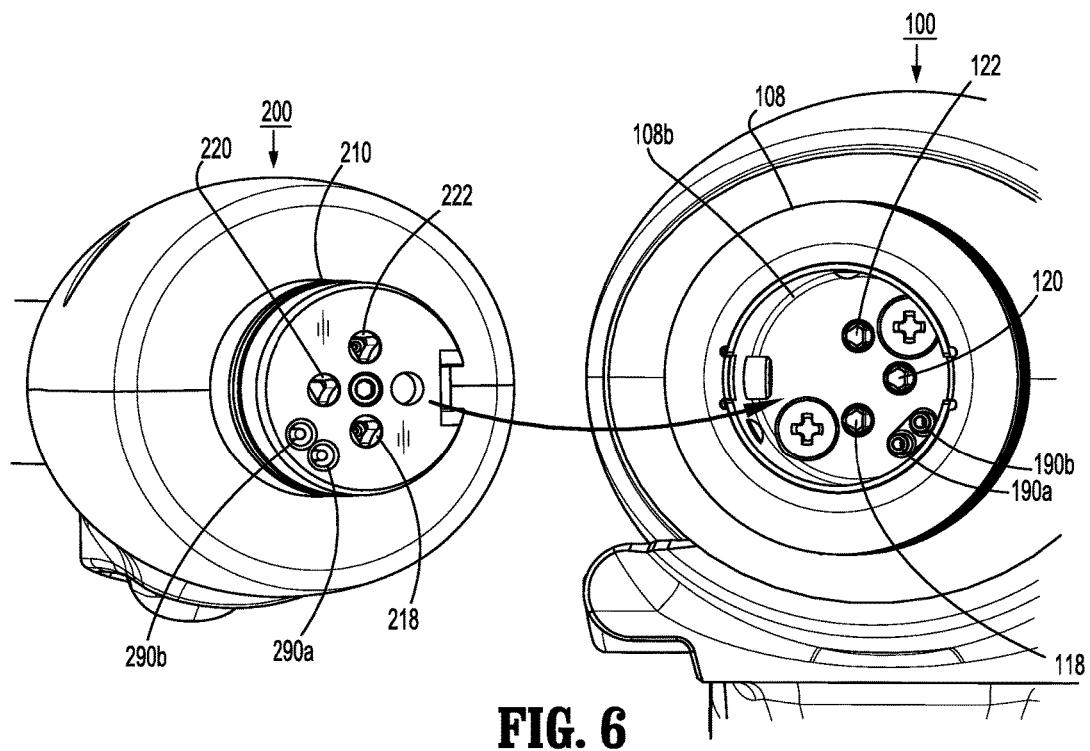
FIG. 6 is a front, perspective view of the surgical instrument of FIG. 1 with the adapter assembly separated therefrom, according to the present disclosure.

With continued reference to FIGS. 3 and 5, distal half-section 110a of upper housing portion 108 defines a nose or connecting portion 108a. A nose cone 114 is supported on nose portion 108a of upper housing portion 108 (FIG. 6). Nose cone 114 is fabricated from a transparent, light-transmissive material. An illumination member 116 is disposed within nose cone 114 such that illumination member 116 is visible therethrough. The nose cone 114 may be tinted, such that the illumination member 116 is visible when it is activated.

With reference to FIG. 5, the illumination member 116 may include a plurality of any suitable light emitting devices, such as light emitting diodes (LEDs), disposed on printed circuit board (LED PCB) 116a which is disposed in a vertical plane transverse to the longitudinal axis "X-X." The illumination member 116 is configured to illuminate in multiple colors with a specific color pattern being associated with a unique discrete event. In embodiments, the LEDs may be single-color or multi-color LEDs.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 relative to proximal body portion 302 of end effector 300, to rotate end effector 300 about the longitudinal axis "X-X" (FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter assembly 200. Proximal to the selector gearbox assembly 162 is a function selection module 163 having a first (e.g., selector) motor 164 that functions to selectively move gear elements within the selector gearbox assembly 162 into engagement with an input drive component 165 having a second (e.g., drive) motor 166.

As illustrated in FIGS. 1-4, distal half-section 110a of upper housing portion 108 defines a connecting portion 108a configured to accept a corresponding drive coupling assembly 210 of adapter assembly 200.

Figure 7:
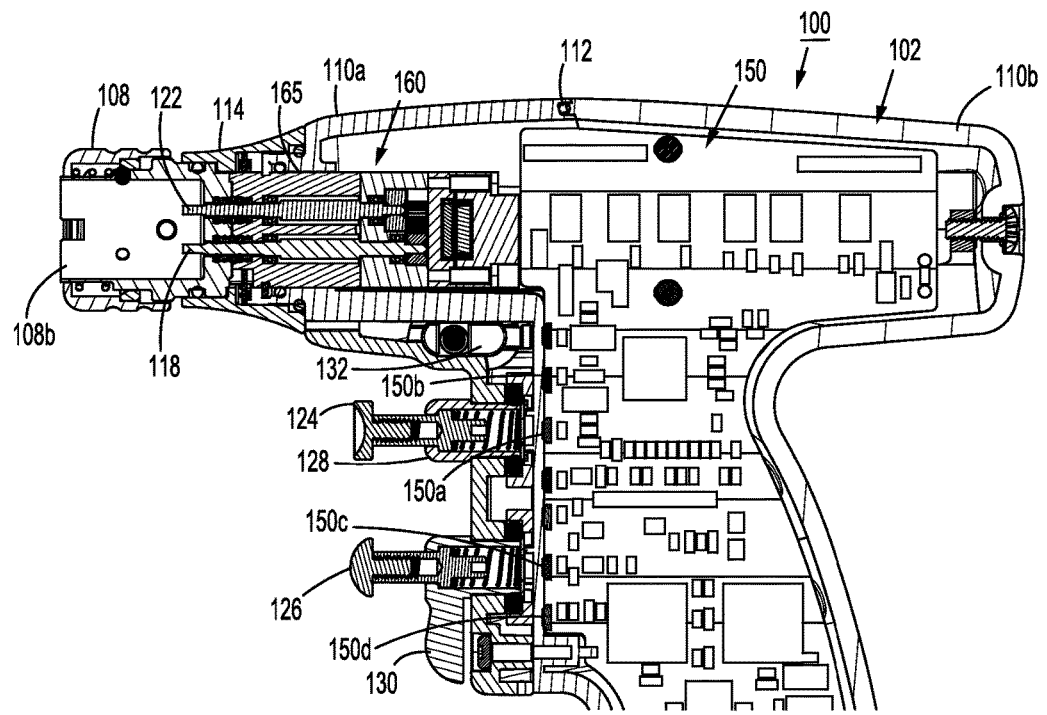
FIG. 7 is a side, cross-sectional view of the surgical instrument of FIG. 1, as taken through 7-7 of FIG. 1, according to the present disclosure.
Figure 8:
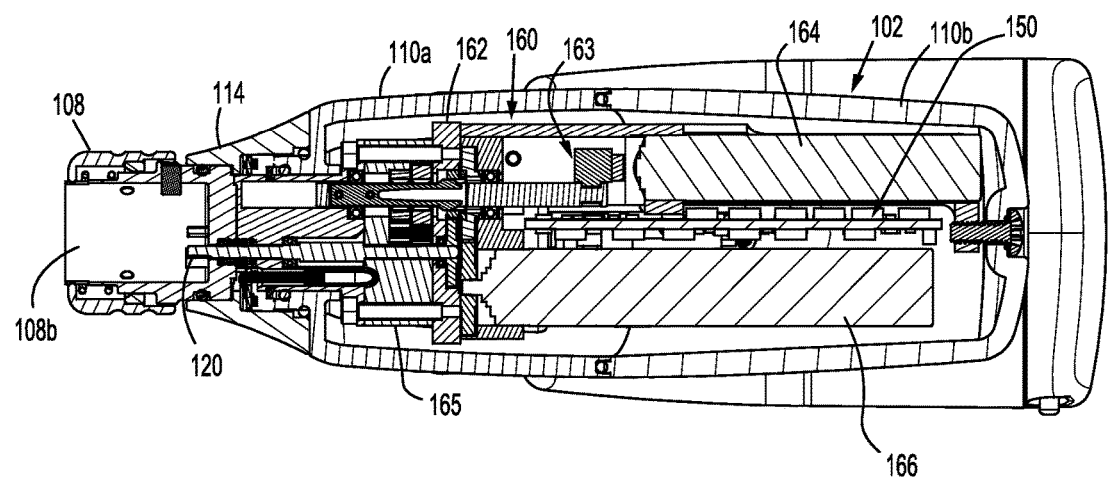
FIG. 8 is a top, cross-sectional view of the surgical instrument of FIG. 1, as taken through 8-8 of FIG. 1, according to the present disclosure.
Figure 9:
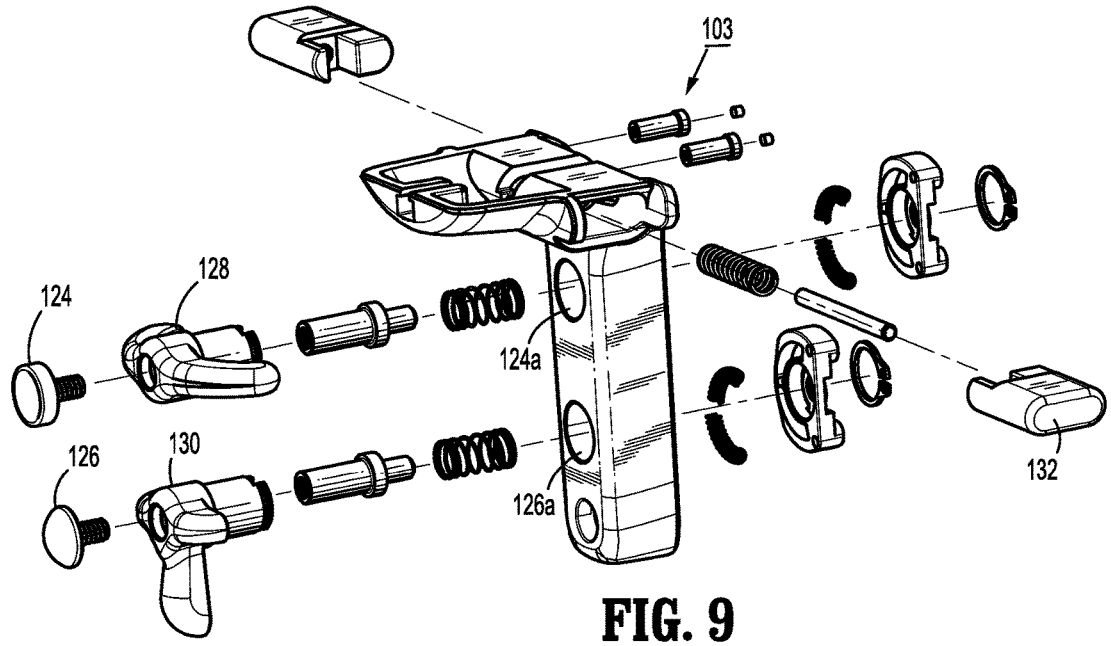
FIG. 9 is a perspective, exploded view of a control assembly of the surgical instrument of FIG. 1, according to the present disclosure.

As illustrated in FIGS. 6-8, connecting portion 108a of surgical instrument 100 has a cylindrical recess 108b that receives a drive coupling assembly 210 of adapter assembly 200 when adapter assembly 200 is mated to surgical instrument 100. Connecting portion 108a houses three rotatable drive connectors 118, 120, 122.

With reference to FIG. 6, when adapter assembly 200 is mated to surgical instrument 100, each of rotatable drive connectors 118, 120, 122 of surgical instrument 100 couples with a corresponding rotatable connector sleeve 218, 220, 222 of adapter assembly 200. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter assembly 200.

The mating of drive connectors 118, 120, 122 of surgical instrument 100 with connector sleeves 218, 220, 222 of adapter assembly 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160.

Since each of drive connectors 118, 120, 122 of surgical instrument 100 has a keyed and/or substantially non-rotatable interface with respective connector sleeves 218, 220, 222 of adapter assembly 200, when adapter assembly 200 is coupled to surgical instrument 100, rotational force(s) are selectively transferred from drive mechanism 160 of surgical instrument 100 to adapter assembly 200.

The selective rotation of drive connector(s) 118, 120 and/or 122 of surgical instrument 100 allows surgical instrument 100 to selectively actuate different functions of end effector 300. As discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 about an articulation axis that is transverse to longitudinal axis "X-X" (FIG. 2). In particular, the end effector 300 defines a second longitudinal axis and is movable from a first position in which the second longitudinal axis is substantially aligned with the first longitudinal axis "X-X" to at least a second position in which the second longitudinal axis is disposed at a non-zero angle with respect to the first longitudinal axis "X-X." Additionally, the selective and independent rotation of third drive connector 122 of surgical instrument 100 corresponds to the selective and independent rotation of end effector 300 about longitudinal axis "X-X" (FIG. 2) relative to handle housing 102 of surgical instrument 100.

As illustrated in FIGS. 1-3 and FIG. 9, handle housing 102 supports a control assembly 103 on a distal surface or side of intermediate housing portion 108. Control assembly 103, in cooperation with intermediate housing portion 108, supports a pair of finger-actuated control buttons 124, 126 and rocker devices 128, 130. In particular, control assembly 103 defines an upper aperture 124a for slidably receiving a first control button 124, and a lower aperture 126a for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150a-150d (FIG. 7) that are actuated by the movement of the magnets in the control buttons 124, 126 and rocker devices 128, 130. In particular, located immediately proximal to the control button 124 is a first Hall-effect switch 150a (FIGS. 3 and 7) that is actuated upon the movement of a magnet within the control button 124 upon the operator actuating control button 124. The actuation of first Hall-effect switch 150a, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second Hall-effect switch 150b (FIGS. 3 and 7) that is actuated upon the movement of a magnet (not shown) within rocker device 128 upon the operator actuating rocker device 128. The actuation of second Hall-effect switch 150b, corresponding to rocker device 128, causes circuit board 150 to provide appropriate signals to function selection module 163 and input drive component 165 of drive mechanism 160 to articulate tool assembly 304 relative to body portion 302 of end effector 300. Advantageously, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

Furthermore, located immediately proximal to control button 126 is a third Hall-effect switch 150c (FIGS. 3 and 7) that is actuated upon the movement of a magnet (not shown) within control button 126 upon the operator actuating control button 126. The actuation of third Hall-effect switch 150c, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fourth Hall-effect switch 150d (FIGS. 3 and 7) that is actuated upon the movement of a magnet (not shown) within rocker device 130 upon the operator actuating rocker device 130. The actuation of fourth Hall-effect switch 150d, corresponding to rocker device 130, causes circuit board 150 to provide appropriate signals to function selection module 163 and input drive component 165 of drive mechanism 160 to rotate end effector 300 relative to handle housing 102 surgical instrument 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As seen in FIGS. 1-3, surgical instrument 100 includes a fire button or safety switch 132 supported between intermediate housing portion 108 and upper housing portion, and situated above control assembly 103. In use, tool assembly 304 of end effector 300 is actuated between opened and closed conditions as needed and/or desired. In order to fire end effector 300, to expel fasteners therefrom when tool assembly 304 of end effector 300 is in a closed condition, safety switch 132 is depressed thereby instructing surgical instrument 100 that end effector 300 is ready to expel fasteners therefrom.

As illustrated in FIGS. 1 and 10-20, surgical instrument 100 is configured for selective connection with adapter assembly 200, and, in turn, adapter assembly 200 is configured for selective connection with end effector 300.

Figure 29:
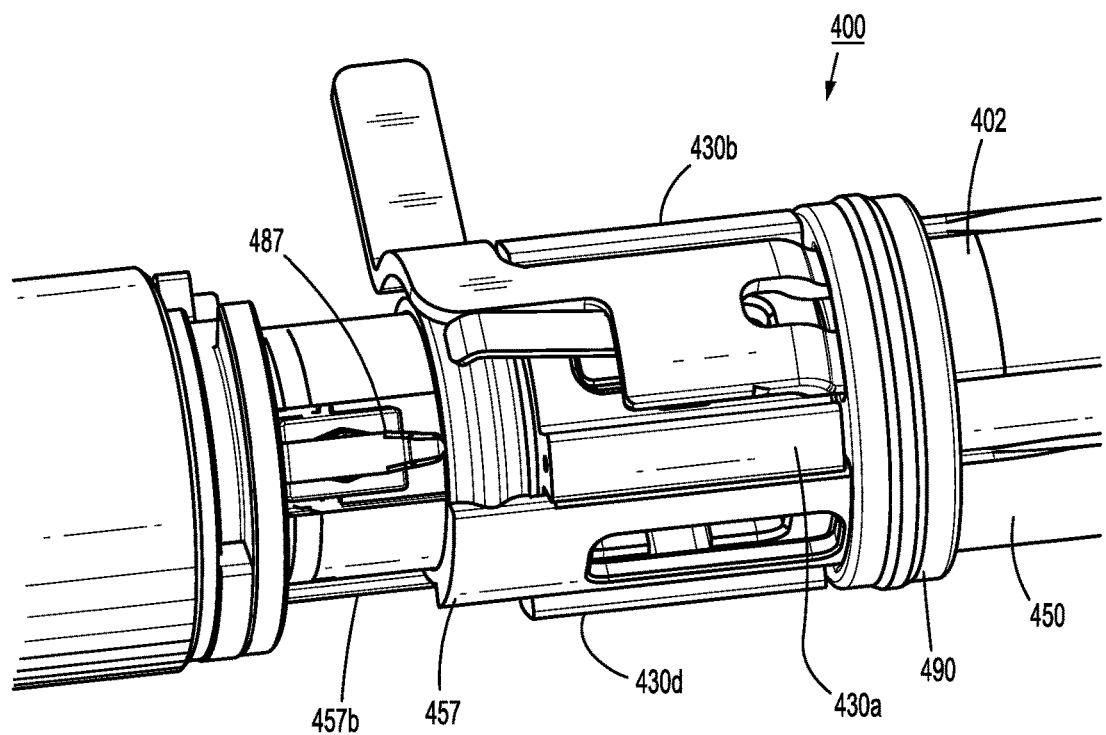
FIG. 29 is an enlarged, perspective, partially-disassembled view of a proximal portion of the adapter assembly of FIG. 1 in an unloaded configuration, according to the present disclosure.

Adapter assembly 200 is configured to convert a rotation of either of drive connectors 120 and 122 of surgical instrument 100 into axial translation useful for operating a drive assembly 360 and an articulation link 366 of end effector 300, as illustrated in FIG. 29 and discussed in greater detail below.

Adapter assembly 200 includes a first drive transmitting assembly for interconnecting third rotatable drive connector 122 of surgical instrument 100 and a first axially translatable drive member of end effector 300, wherein the first drive transmitting assembly converts and transmits a rotation of third rotatable drive connector 122 of surgical instrument 100 to an axial translation of the first axially translatable drive assembly 360 of end effector 300 for firing.

Adapter assembly 200 includes a second drive transmitting assembly for interconnecting second rotatable drive connector 120 of surgical instrument 100 and a second axially translatable drive member of end effector 300, wherein the second drive transmitting assembly converts and transmits a rotation of second rotatable drive connector 120 of surgical instrument 100 to an axial translation of articulation link 366 of end effector 300 for articulation.

Figure 10:
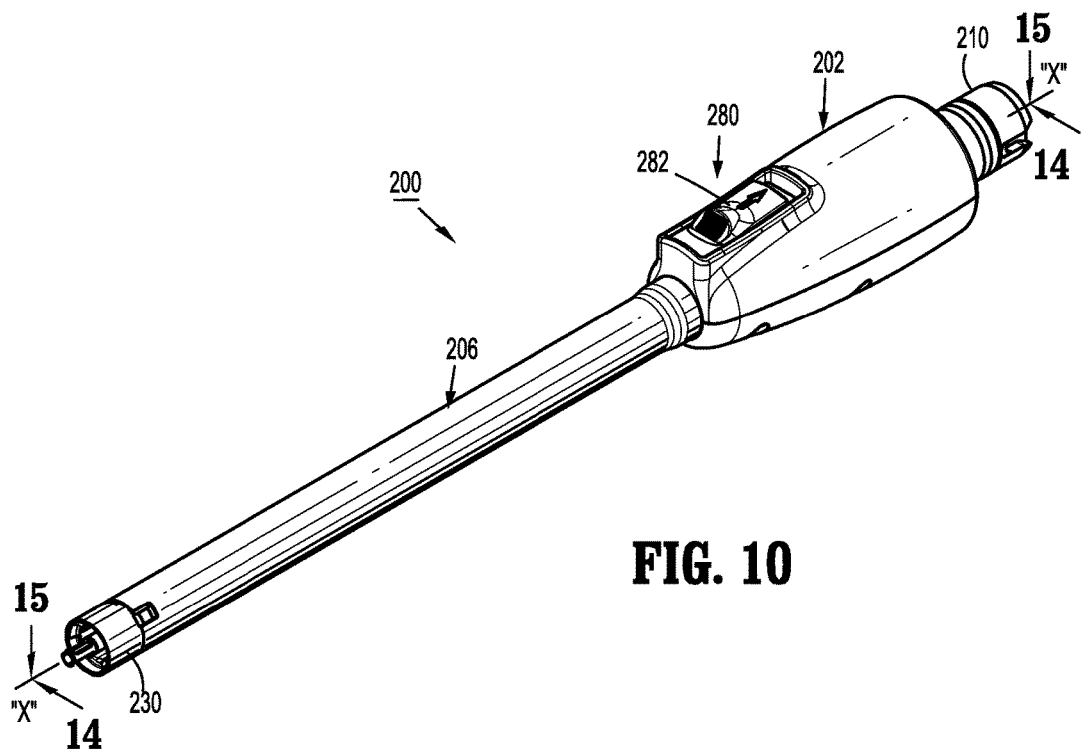
FIG. 10 is a perspective view of the adapter assembly of FIG. 1, according to the present disclosure.
Figure 11:
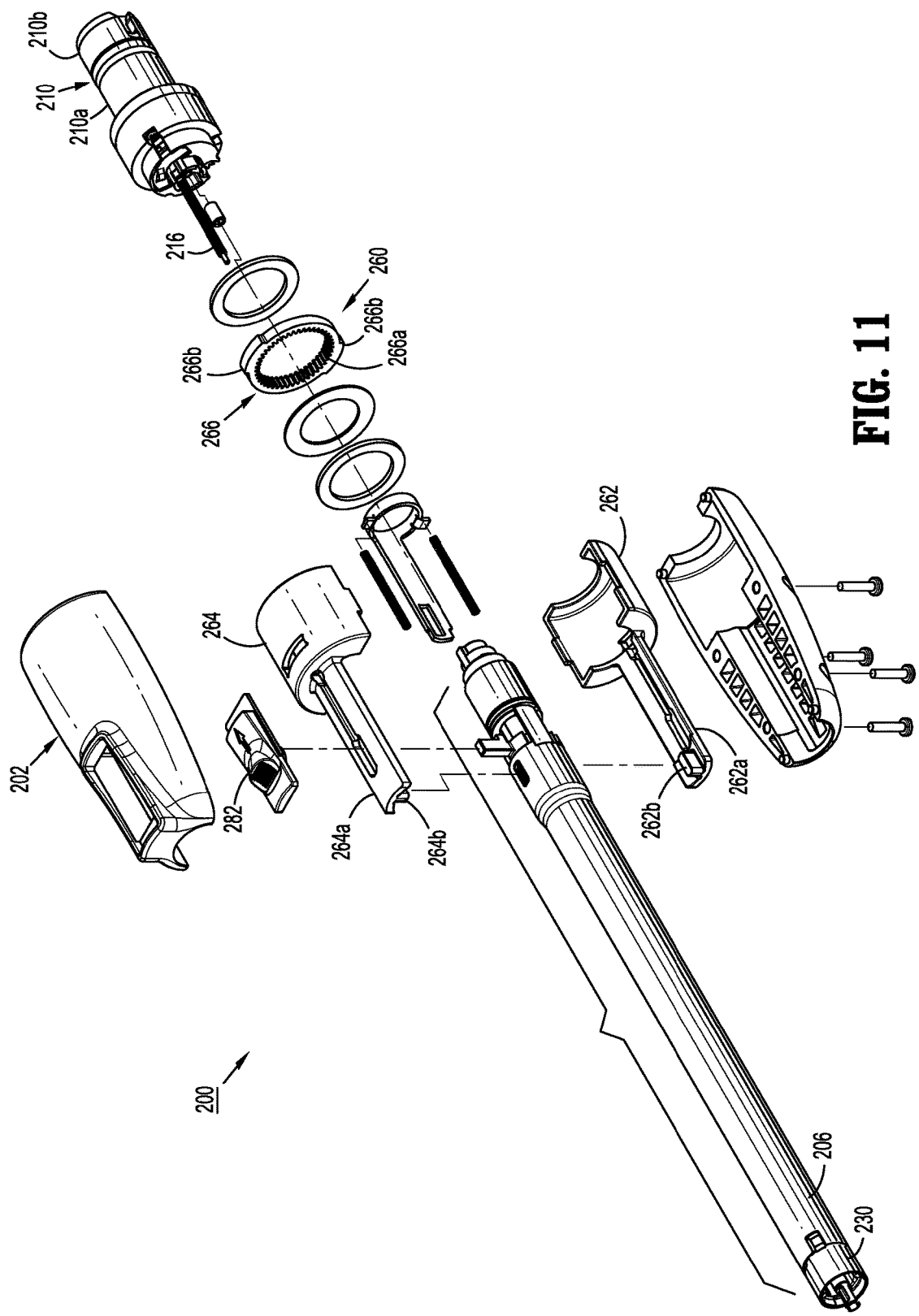
FIG. 11 is a perspective, exploded view of the adapter assembly of FIG. 1, according to the present disclosure.

With reference to FIGS. 10 and 11, adapter assembly 200 includes a knob housing 202 and an outer tube 206 extending from a distal end of knob housing 202. Knob housing 202 and outer tube 206 are configured and dimensioned to house the components of adapter assembly 200. Outer tube 206 is dimensioned such that outer tube 206 is passable through a typical trocar port, cannula or the like. Knob housing 202 is dimensioned to not enter the trocar port, cannula of the like.

Figure 12:
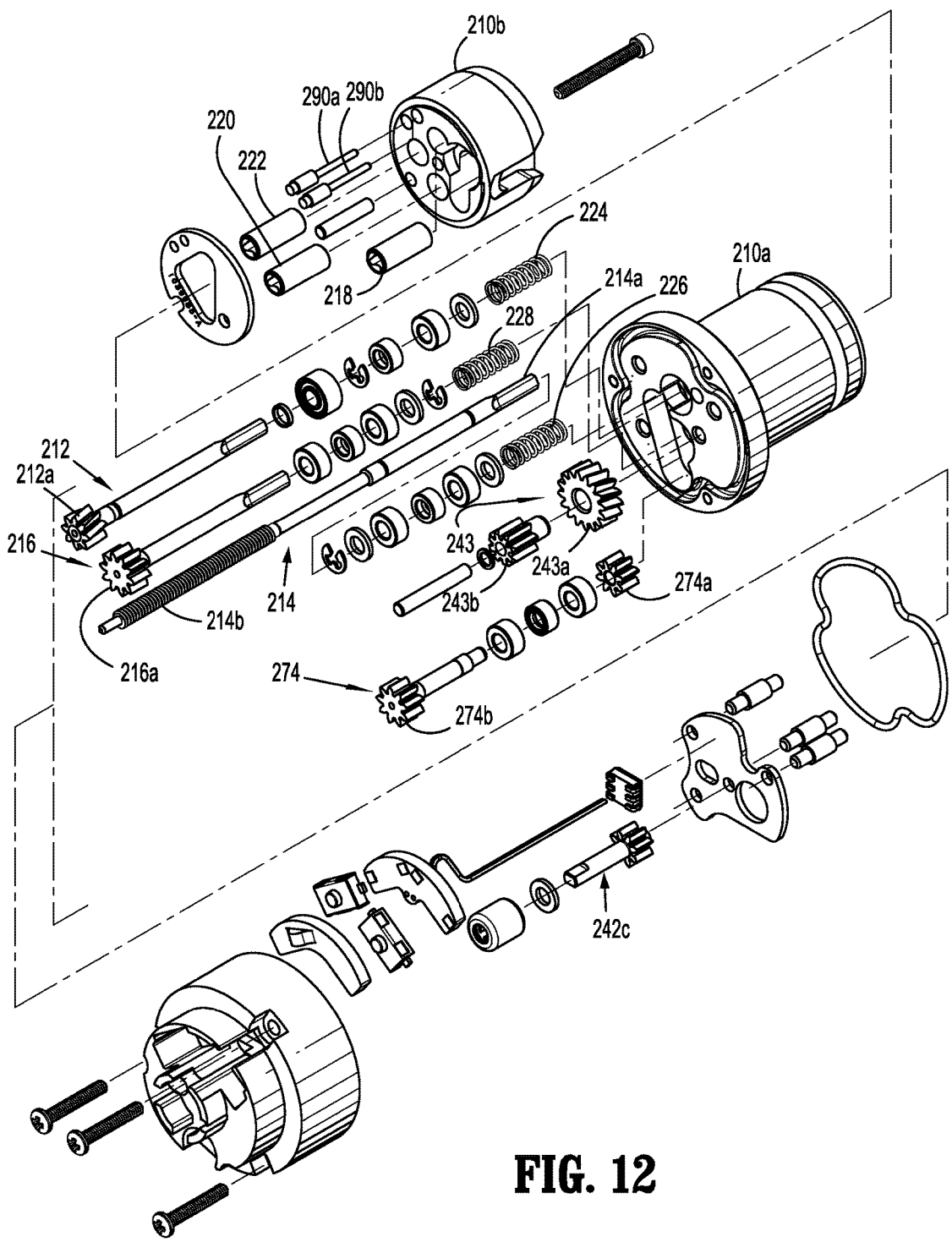
FIG. 12 is a perspective, exploded view of a coupling assembly of the adapter assembly of FIG. 1, according to the present disclosure.
Figure 13:
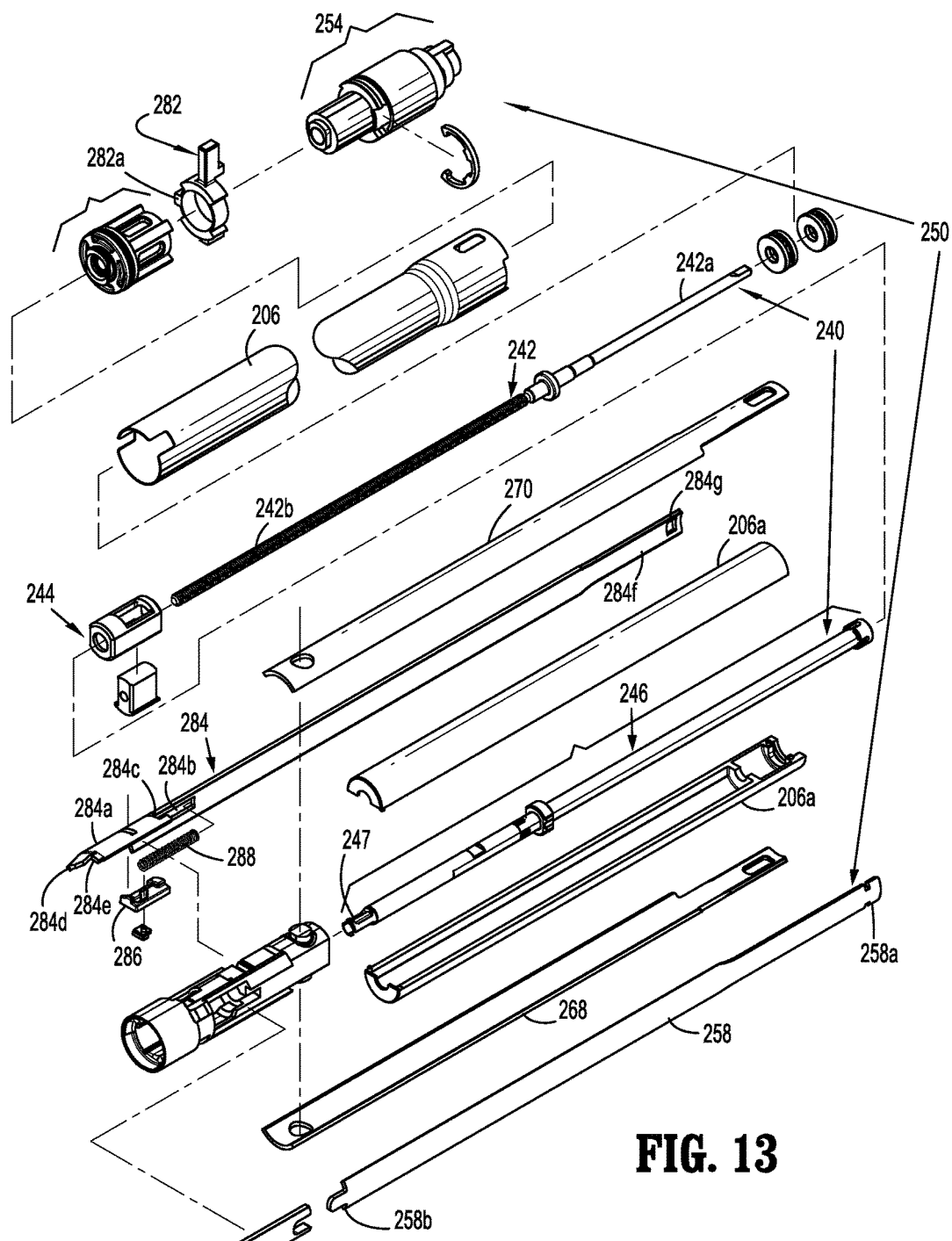
FIG. 13 is a perspective, exploded view of a drive transmitting assembly of the adapter assembly of FIG. 1, according to the present disclosure.
Figure 14:
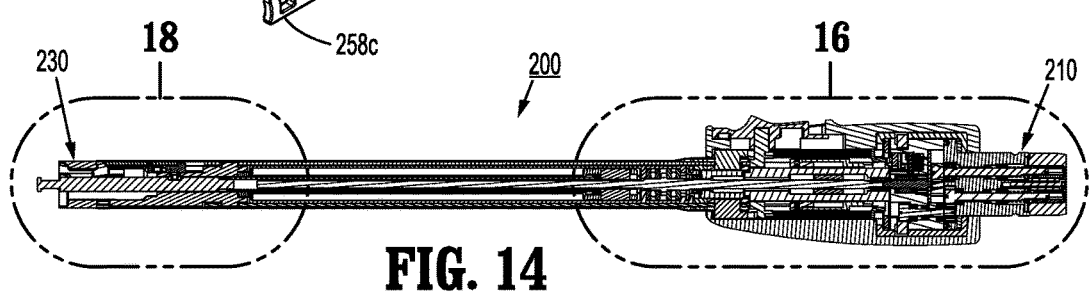
FIG. 14 is a side, cross-sectional view of the adapter assembly of FIG. 1, according to the present disclosure.
Figure 15:
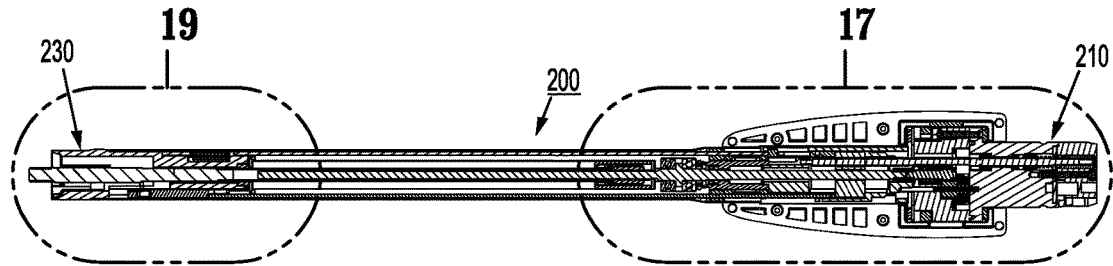
FIG. 15 is a top, cross-sectional view of the adapter assembly of FIG. 1, according to the present disclosure.
Figure 16:
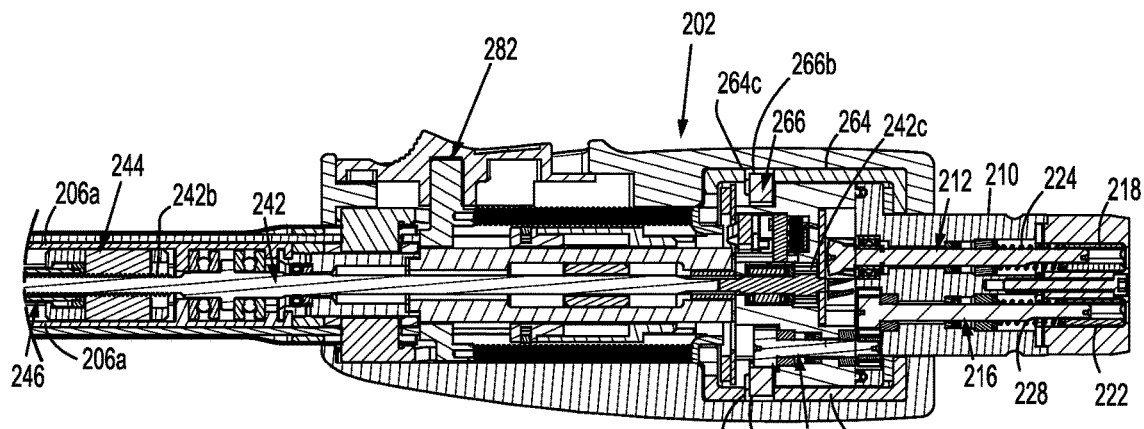
FIG. 16 is an enlarged, side, cross-sectional view of a proximal area of detail of the adapter assembly of FIG. 1, according to the present disclosure.
Figure 17:
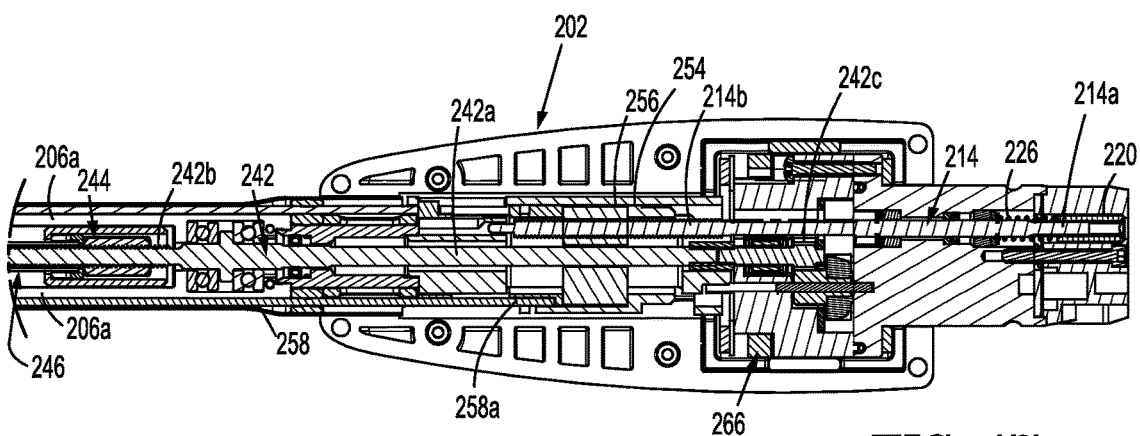
FIG. 17 is an enlarged, top, cross-sectional view of the proximal area of detail of the adapter assembly of FIG. 1, according to the present disclosure.
Figure 18:
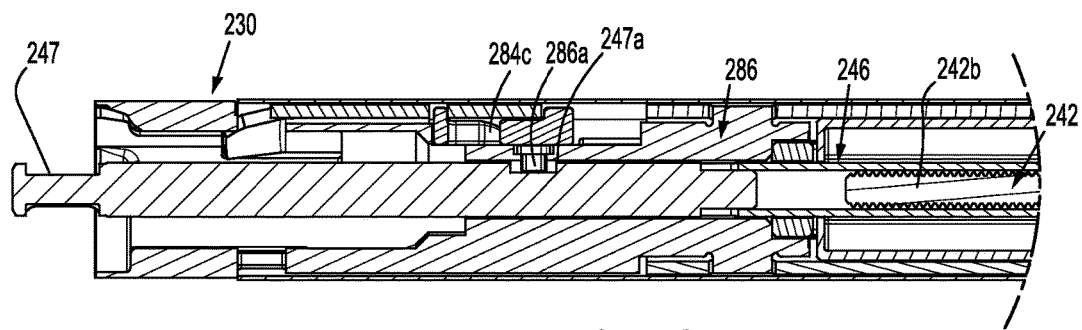
FIG. 18 is an enlarged, side, cross-sectional view of a distal area of detail of the adapter assembly of FIG. 1, according to the present disclosure.
Figure 19:
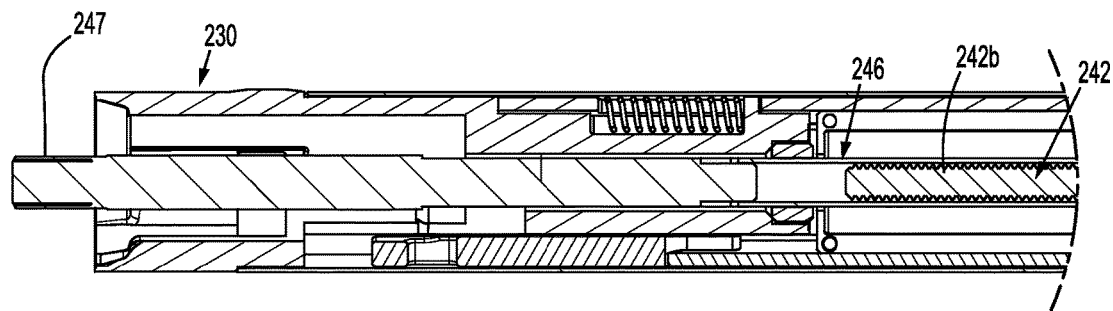
FIG. 19 is an enlarged, top, cross-sectional view of the distal area of detail of the adapter assembly of FIG. 1, according to the present disclosure.

Knob housing 202 is configured and adapted to connect to connecting portion 108a of upper housing portion 108 of distal half-section 110a of surgical instrument 100. With reference to FIGS. 10-12, adapter assembly 200 includes a surgical device drive coupling assembly 210 at a proximal end thereof and to an end effector coupling assembly 230 at a distal end thereof. Drive coupling assembly 210 includes a distal drive coupling housing 210a and a proximal drive coupling housing 210b rotatably supported, at least partially, in knob housing 202. Drive coupling assembly 210 rotatably supports a first rotatable proximal drive shaft 212, a second rotatable proximal drive shaft 214, and a third rotatable proximal drive shaft 216 therein.

Proximal drive coupling housing 210b is configured to rotatably support first, second and third connector sleeves 218, 220 and 222, respectively. Each of connector sleeves 218, 220, 222 is configured to mate with respective first, second and third drive connectors 118, 120, 122 of surgical instrument 100, as described above. Each of connector sleeves 218, 220, 222 is further configured to mate with a proximal end of respective first, second and third proximal drive shafts 212, 214, 216.

Proximal drive coupling assembly 210 includes a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216.

Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical instrument 100 when adapter assembly 200 is connected to surgical instrument 100.

In particular, first, second and third biasing members 224, 226 and 228 bias respective connector sleeves 218, 220 and 222 in a proximal direction. In this manner, during assembly of adapter assembly 200 to surgical instrument 100, if first, second and or third connector sleeves 218, 220 and/or 222 is/are misaligned with the drive connectors 118, 120, 122 of surgical instrument 100, first, second and/or third biasing member(s) 224, 226 and/or 228 are compressed. Thus, when drive mechanism 160 of surgical instrument 100 is engaged, drive connectors 118, 120, 122 of surgical instrument 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical instrument 100 to first, second and/or third proximal drive shaft(s) 212, 214 and 216 of proximal drive coupling assembly 210.

Upon calibration of surgical instrument 100, each of drive connectors 118, 120, 122 of surgical instrument 100 is rotated and biasing of connector sleeve(s) 218, 220 and 222 properly seats connector sleeve(s) 218, 220 and 222 over the respective drive connectors 118, 120, 122 of surgical instrument 100 when the proper alignment is reached.

Adapter assembly 200 includes a first, a second and a third drive transmitting assembly 240, 250, 260, respectively, disposed within handle housing 202 and outer tube 206. Each drive transmitting assembly 240, 250, 260 is configured and adapted to transmit or convert a rotation of a first, second and third drive connector 118, 120, 122 of surgical instrument 100 into axial translation of drive tube 246 and drive bar 258 of adapter assembly 200, to effectuate closing, opening, articulating and firing of end effector 300; or a rotation of ring gear 266 of adapter assembly 200, to effectuate rotation of adapter assembly 200.

As shown in FIGS. 13-19, first drive transmitting assembly 240 includes a first distal drive shaft 242 rotatably supported within housing 202 and outer tube 206. A proximal end portion 242a of first distal drive shaft 242 is keyed to a spur gear 242c which is configured for connection to a spur gear 212a keyed to first rotatable proximal drive shaft 212, via a compound gear 243. First distal drive shaft 242 further includes a distal end portion 242b having a threaded outer profile or surface.

First drive transmitting assembly 240 further includes a drive coupling nut 244 rotatably coupled to threaded distal end portion 242b of first distal drive shaft 242, and which is slidably disposed within outer tube 206. Drive coupling nut 244 is keyed to an inner housing tube 206a of outer tube 206 so as to be prevented from rotation as first distal drive shaft 242 is rotated. In this manner, as first distal drive shaft 242 is rotated, drive coupling nut 244 is translated through and/or along inner housing tube 206a of outer tube 206.

First drive transmitting assembly 240 further includes a drive tube 246 surrounding first distal drive shaft 242 and having a proximal end portion connected to drive coupling nut 244 and a distal end portion extending beyond a distal end of first distal drive shaft 242. The distal end portion of drive tube 246 supports a connection member 247 (FIG. 13) configured and dimensioned for selective engagement with drive member 374 of drive assembly 360 of end effector 300.

In operation, as first rotatable proximal drive shaft 212 is rotated, due to a rotation of first connector sleeve 218, as a result of the rotation of the first respective drive connector 118 of surgical instrument 100, spur gear 212a of first rotatable proximal drive shaft 212 engages first gear 243a of compound gear 243 causing compound gear 243 to rotate. As compound gear 243 rotates, a second gear 243b of compound gear 243 is rotated and thus causes spur gear 242c that is keyed to first distal drive shaft 242, that is engaged therewith, to also rotate thereby causing first distal drive shaft 242 to rotate. As first distal drive shaft 242 is rotated, drive coupling nut 244 is caused to be translated axially along first distal drive shaft 242.

As drive coupling nut 244 is caused to be translated axially along first distal drive shaft 242, drive tube 246 is caused to be translated axially relative to inner housing tube 206a of outer tube 206. As drive tube 246 is translated axially, with connection member 247 connected thereto and connected to a drive member 374 of drive assembly 360 of end effector 300, drive tube 246 causes concomitant axial translation of drive member 374 of end effector 300 to effectuate a closure of tool assembly 304 and a firing of tool assembly 304 of end effector 300.

With reference to FIGS. 13-19, second drive transmitting assembly 250 of adapter assembly 200 includes second rotatable proximal drive shaft 214 rotatably supported within drive coupling assembly 210. Second rotatable proximal drive shaft 214 includes a non-circular or shaped proximal end portion 214a configured for connection with second connector 220 which is connected to respective second connector 120 of surgical instrument 100. Second rotatable proximal drive shaft 214 further includes a distal end portion 214b having a threaded outer profile or surface.

Figure 20:
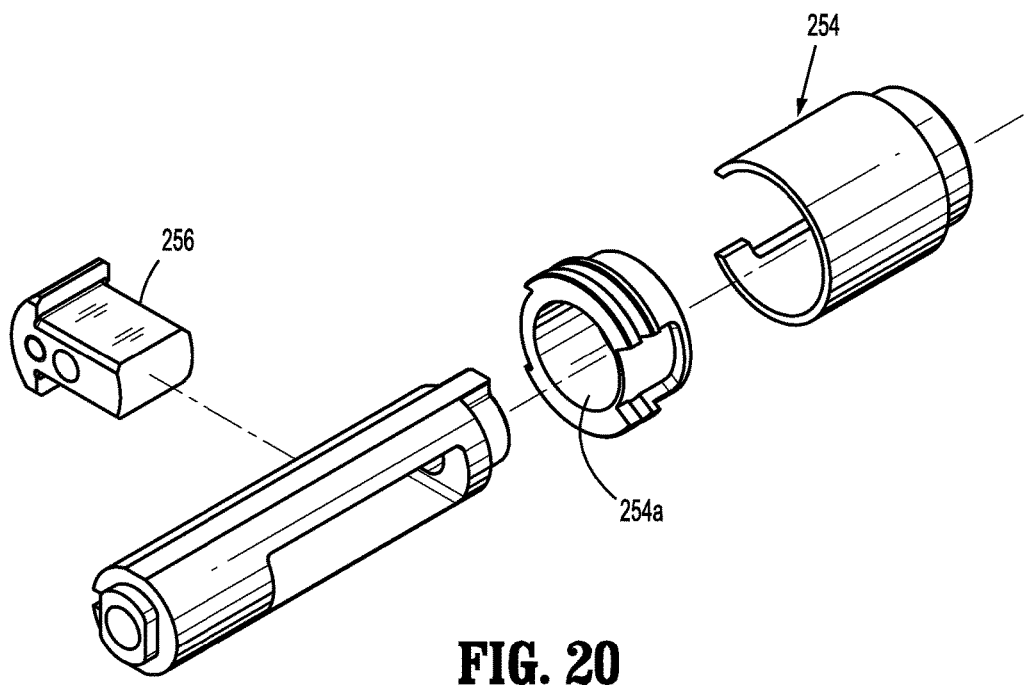
FIG. 20 is an enlarged perspective view, with parts separated, of a coupling cuff of the adapter assembly illustrated in FIG. 13.

As illustrated in FIG. 20, second drive transmitting assembly 250 further includes a coupling cuff 254 rotatably and translatably supported within an annular race or recess formed in knob housing 202. Coupling cuff 254 defines a lumen 254a therethrough, and an annular race or recess formed in a surface of lumen 254a. Second drive transmitting assembly 250 further includes a coupling slider 256 extending across lumen 254a of coupling cuff 254 and slidably disposed within the race of coupling cuff 254. Coupling slider 256 is threadably connected to threaded distal end portion 214b of second rotatable proximal drive shaft 214. As so configured, coupling cuff 254 can rotate about second rotatable proximal drive shaft 214, thereby maintaining a radial position of second rotatable proximal drive shaft 214 relative to first rotatable proximal drive shaft 242.

Second rotatable proximal drive shaft 214 defines an axis of rotation, and coupling cuff 254 defines an axis of rotation that is spaced a radial distance from the axis of rotation of second rotatable proximal drive shaft 214. Coupling slider 256 defines an axis of rotation that is coincident with the axis of rotation of coupling cuff 254.

Second drive transmitting assembly 250 further includes a drive bar 258 translatably supported for axial translation through outer tube 206. Drive bar 258 includes a proximal end portion 258a coupled to coupling cuff 254, and a distal end portion 258b defining a coupling hook 258c configured and dimensioned for selective engagement with hooked proximal end 366a of articulation link 366 of end effector 300 (FIG. 29).

In operation, as illustrated in FIGS. 10-19, as drive shaft 214 is rotated due to a rotation of second connector sleeve 220, as a result of the rotation of the second drive connector 120 of surgical instrument 100, coupling slider 256 is caused to be translated axially along threaded distal portion 214b of second rotatable proximal drive shaft 214, which in turn causes coupling cuff 254 to be translated axially relative to knob housing 202. As coupling cuff 254 is translated axially, drive bar 258 is caused to be translated axially. Accordingly, as drive bar 258 is translated axially, with hook 258c thereof connected to hooked proximal end 366a of articulation link 366 of end effector 300 (FIG. 29), drive bar 258 causes concomitant axial translation of articulation link 366 of end effector 300 to effectuate an articulation of tool assembly 304.

As seen in FIGS. 10-19, adapter assembly 200 includes a third drive transmitting assembly 260 supported in knob housing 202. Third drive transmitting assembly 260 includes first and second rotation housing half-sections 262, 264 rotatably supported in knob housing 202, respectively, and an internal rotation ring gear 266 supported and interposed between first and second rotation housing half-sections 262, 264. Each of first and second rotation housing half-sections 262, 264 includes an arm 262a, 264b extending distally therefrom and which are parallel to one another and spaced a transverse distance from one another. Each arm 262a, 264a includes a boss 262b, 264b extending radially inward near a distal end thereof.

Third drive transmitting assembly 260 further includes a pair of rotation transmitting bars 268, 270, each, connected at a proximal end thereof to bosses 262b, 264b of arms 262a, 264a, and at a distal end thereof to a distal coupling assembly 230 supported at a distal end of outer tube 206.

Third drive transmitting assembly 260 includes a ring gear 266 defining an internal array of gear teeth 266a. Ring gear 266 includes a pair of diametrically opposed, radially extending protrusions 266b projecting form an outer edge thereof. Protrusions 266b are disposed within recesses 262c, 264c defined in an inner surface of first and second rotation housing half-sections 262, 264, such that rotation of ring gear 266 results in rotation of first and second rotation housing half-sections 262, 264.

Third drive transmitting assembly 260 further includes third rotatable proximal drive shaft 216 rotatably supported within housing 202 and outer tube 206. A proximal end portion of third rotatable proximal drive shaft 216 is keyed to third connector 222 of adapter assembly 200. Third rotatable proximal drive shaft 216 includes a spur gear 216a keyed to a distal end thereof. A gear set 274 inter-engages spur gear 216a of third rotatable proximal drive shaft 216 to gear teeth 266a of ring gear 266. Gear set 274 includes a first gear 274a engaged with spur gear 216a of third rotatable proximal drive shaft 216, and a second gear 274b engaged with gear teeth 266a of ring gear 266.

In operation, as illustrated in FIGS. 10-19, as third rotatable proximal drive shaft 216 is rotated, due to a rotation of third connector sleeve 222, as a result of the rotation of the third respective drive connector 122 of surgical instrument 100, spur gear 216a of third rotatable proximal drive shaft 216 engages first gear 272a of gear set 274 causing gear set 274 to rotate. As gear set 274 rotates, second gear 274b of gear set 274 is rotated and thus causes ring gear 266 to also rotate thereby causing first and second rotation housing half-sections 262, 264 to rotate. As first and second rotation housing half-sections 262, 264 are rotated, rotation transmitting bars 268, 270, and distal coupling assembly 230 connected thereto, are caused to be rotated about longitudinal axis "X-X" of adapter assembly 200 (FIG. 10). As distal coupling 230 is rotated, end effector 300, that is connected to distal coupling assembly 230, is also caused to be rotated about a longitudinal axis of adapter assembly 200.

Figure 21:
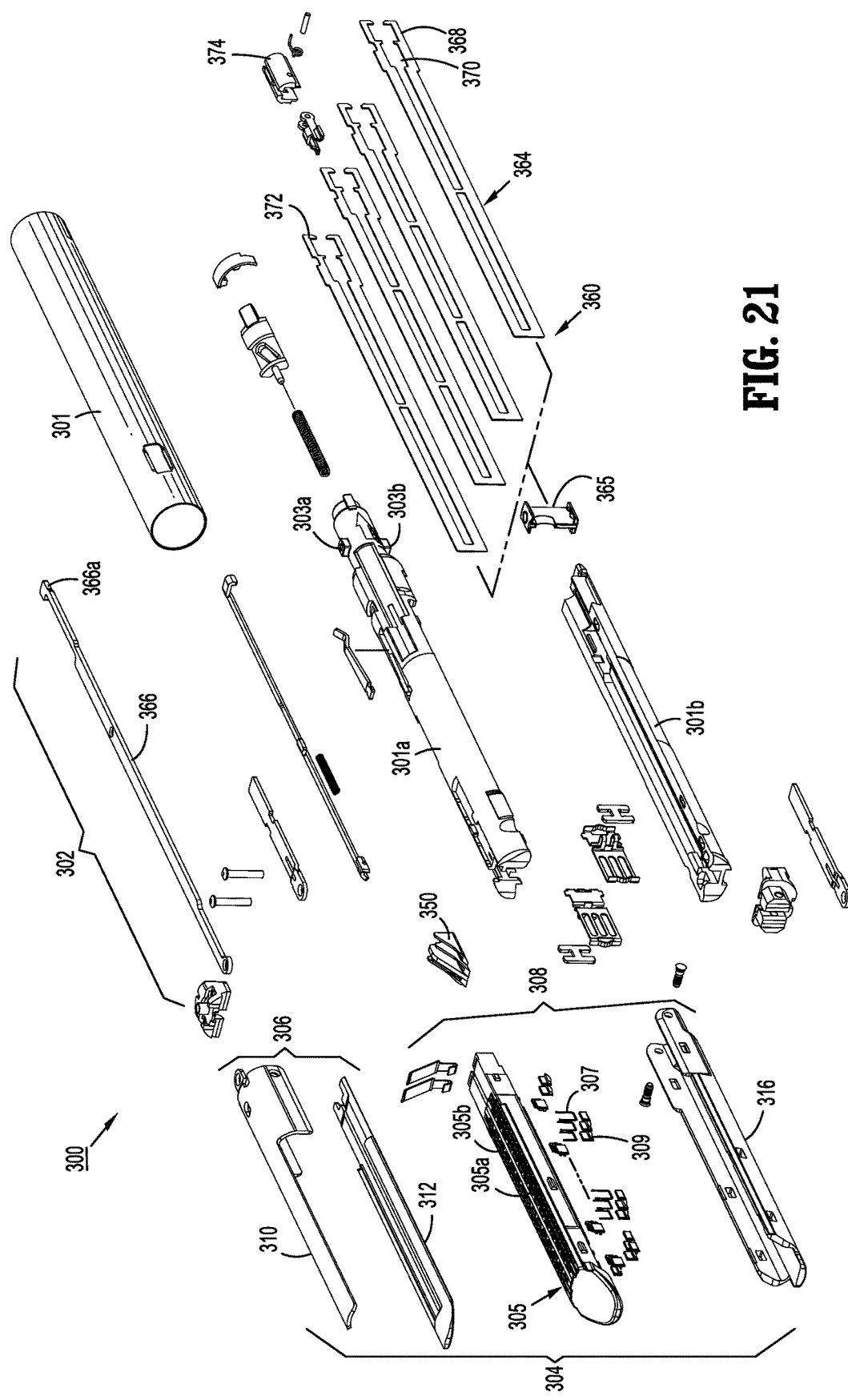
FIG. 21 is a perspective, exploded view of a end effector of FIG. 1, according to the present disclosure.

Referring to FIG. 21, drive assembly 360 of end effector 300 includes a flexible drive shaft 364 having a distal end which is secured to a dynamic drive beam 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of shaft 364. Drive member 374 defines a proximal porthole which receives a connection member of drive tube 246 (FIG. 1) of adapter 200 when end effector 300 is attached to distal coupling 230 of adapter 200.

When drive assembly 360 is advanced distally within tool assembly 304, an upper beam of drive beam 365 moves within a channel defined between anvil plate 312 and anvil cover 310 and a lower beam moves within a channel of the staple cartridge 305 and over the exterior surface of carrier 316 to close tool assembly 304 and fire staples therefrom.

Proximal body portion 302 of end effector 300 includes a sheath or outer tube 301 enclosing an upper housing portion 301a and a lower housing portion 301b. The housing portions 301a and 301b enclose an articulation link 366 having a hooked proximal end 366a which extends from a proximal end of end effector 300. Hooked proximal end 366a of articulation link 366 engages a coupling hook (not shown) of adapter 200 when end effector 300 is secured to distal housing 232 of adapter 200. When drive bar (not shown) of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 21, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of instrument 100, drive assembly 360 abuts an actuation sled 350 and pushes actuation sled 350 through cartridge 305. As the actuation sled moves through cartridge 305, cam wedges of the actuation sled 350 sequentially engage staple pushers 309 to move staple pushers 309 vertically within staple retention slots 305b and sequentially eject a single staple 307 therefrom for formation against anvil plate 312.

The end effector 300 may also include one or more mechanical lockout mechanisms, such as those described in commonly-owned U.S. Pat. Nos. 5,071,052, 5,397,046, 5,413,267, 5,415,335, 5,715,988, 5,718,359, 6,109,500, the entire contents of all of which are incorporated by reference herein.

With reference to FIGS. 22-39, adapter assembly 200 further includes a lock mechanism 400 for fixing the axial position and radial orientation of drive tube 246 (see FIG. 13) for the connection and disconnection of end effector 300 thereto. Lock mechanism 400 includes a release button 282 (see FIG. 13) slidably supported on knob housing 202. Release button 282 is connected to a load link 402 that extends longitudinally through outer tube 206. The lock mechanism 400 also includes a sensor link assembly 451 having a proximal sensor link 450 and a distal sensor link 480. Load link 402 and proximal sensor link 450 are interposed between outer tube 206 and inner housing tubes 206a, 206b and distal tip housing 460. Load link 402 and proximal sensor link 450 move in response to the insertion of end effector 300 and/or movement of lock release button 282. The tip housing 460 is configured and dimensioned for insertion of end effector 300 thereinto as described in further detail below.

The tip housing 460 includes a bayonet connection mount 461 for releasably connecting to the end effector 300. With reference to FIG. 21, the end effector 300 includes a pair of lugs 303a and 303b disposed at a proximal portion of the end effector 300. The lugs 303a and 303b are configured and dimensioned to be inserted into the bayonet connection mount 461 having a pair of corresponding bayonet channels.

Figures 22, 23:
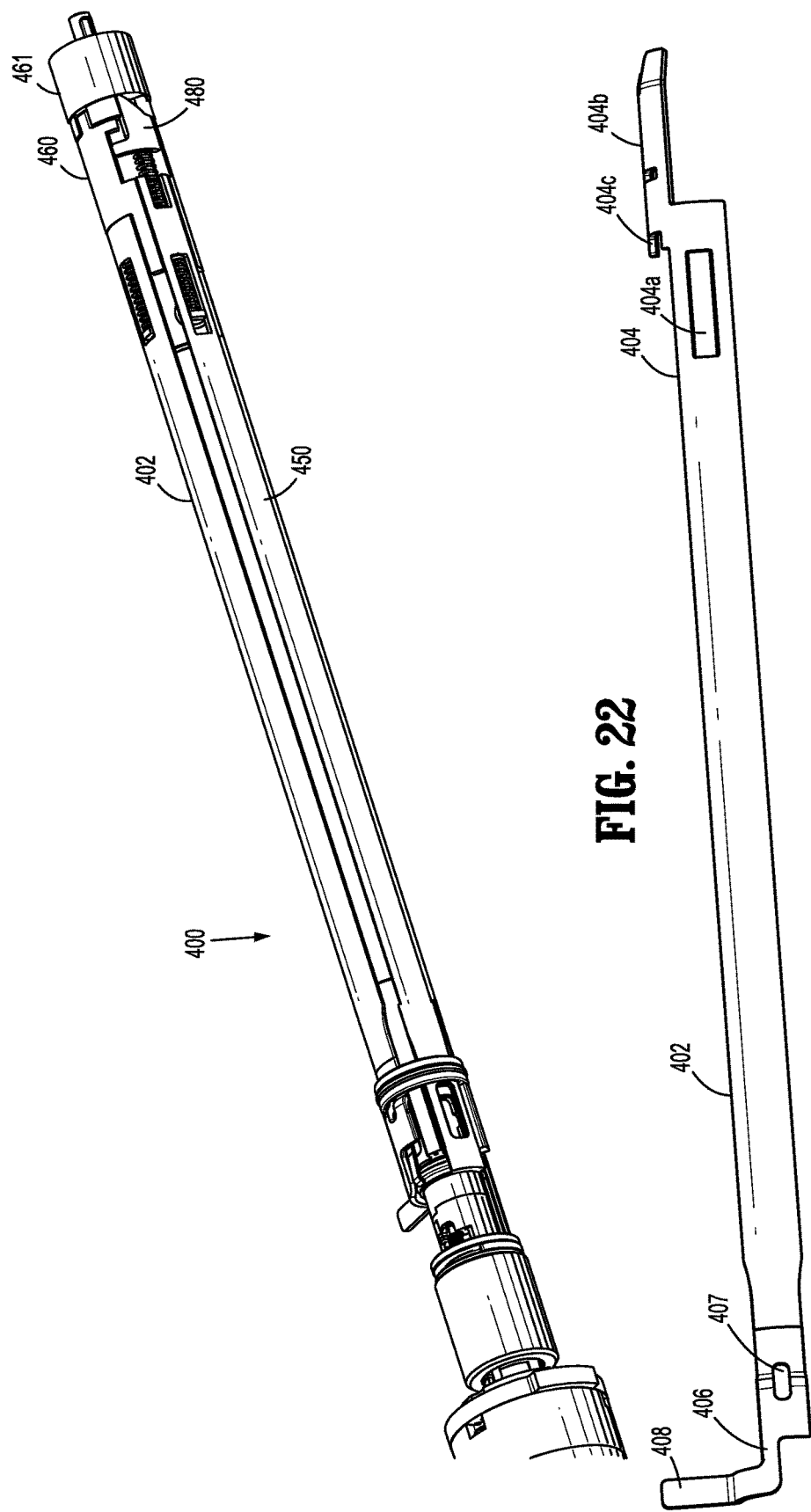
FIG. 22 is a perspective, partially-disassembled view of the adapter assembly of FIG. 1, according to the present disclosure.
FIG. 23 is a perspective view of a load link of the adapter assembly of FIG. 1, according to the present disclosure.
Figure 24:
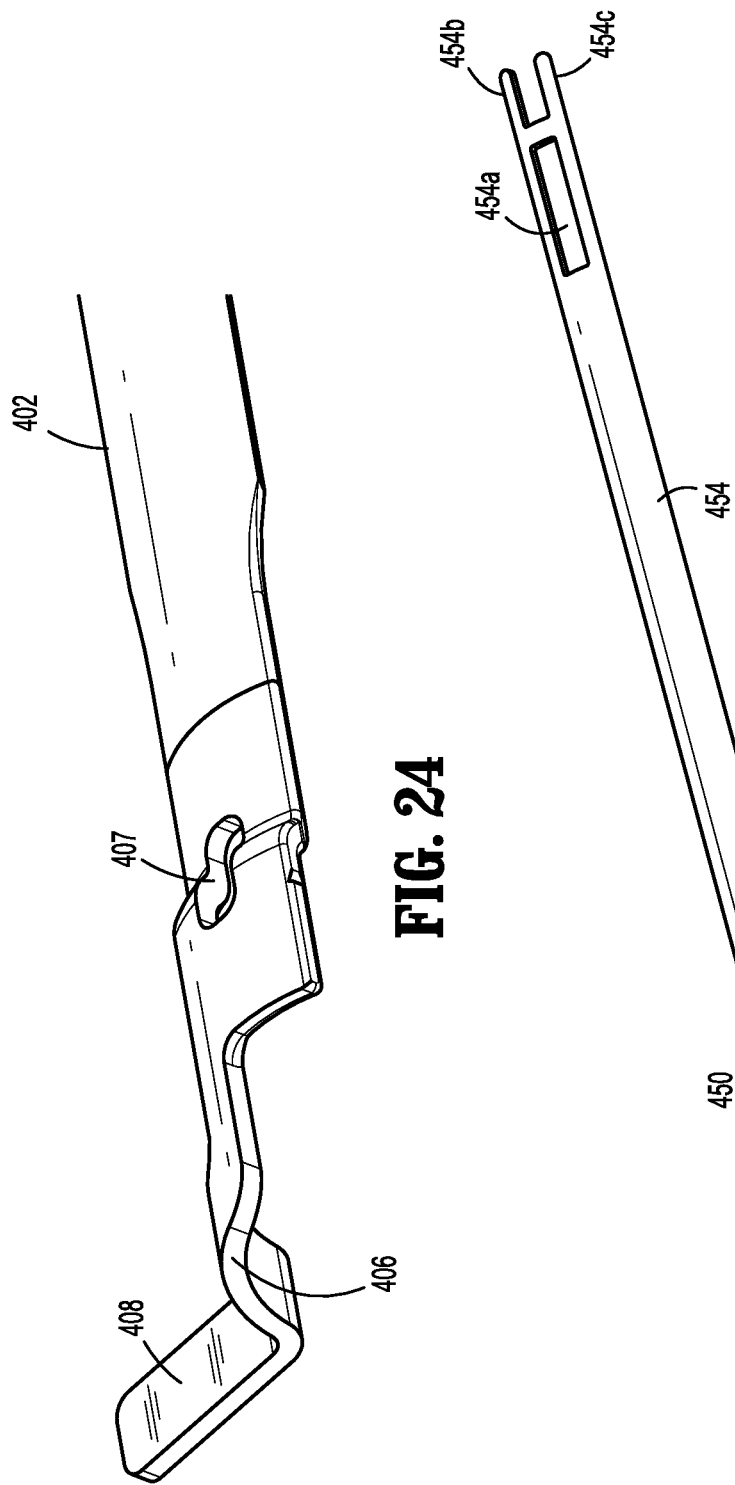
FIG. 24 is a perspective view of a proximal portion of the load link of FIG. 23, according to the present disclosure.

With reference to FIGS. 22-24, load link 402 includes a distal portion 404 defining a cut-out 404a, and a finger 404b extending distally from distal portion 404. The finger 404b of load link 402 includes a distal surface 404c. The load link 402 further includes a proximal portion 406 having an opening 407 configured and dimensioned to engage a lock spring 440 as described in further detail below. The load link 402 further includes a button link 408 configured as a cantilevered tab. The button link 408 is configured and dimensioned to engage the button 282. In use, longitudinal movement (e.g., proximal) of the button 282 is imparted to the load link 402 via the button link 408 thereby allowing for disengagement of the end effector 300 from the adapter 200.

Figure 25:
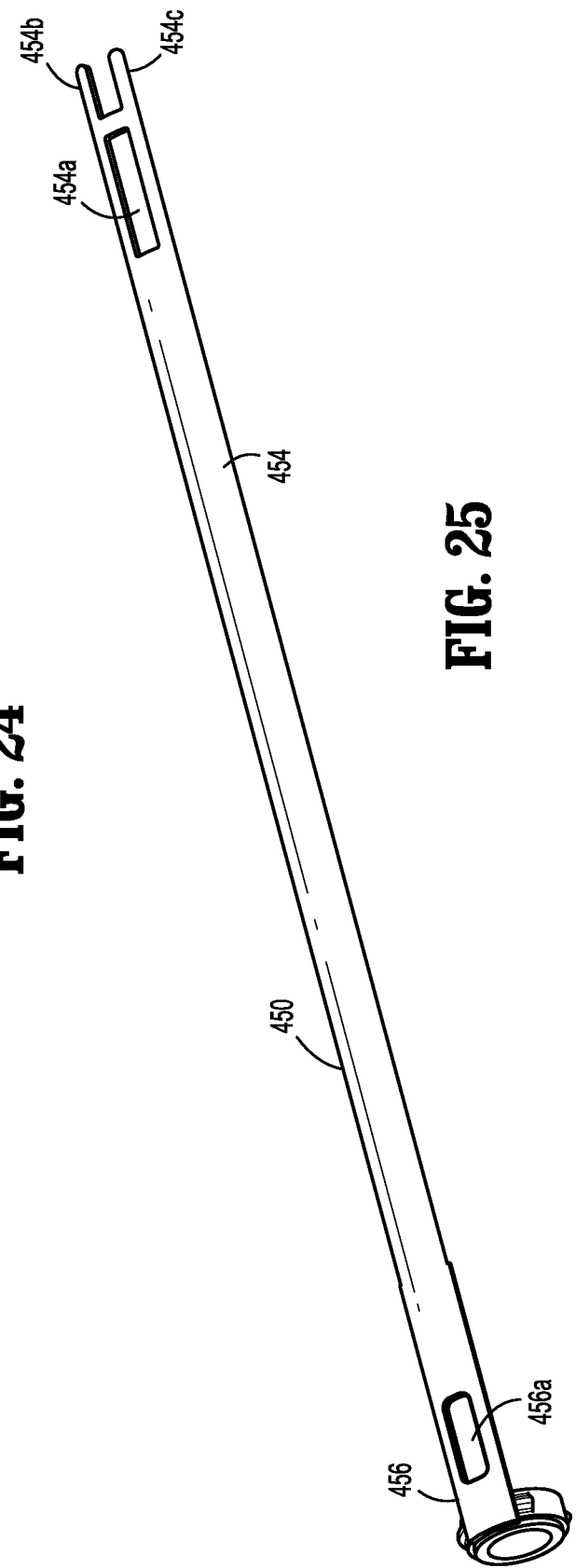
FIG. 25 is a perspective view of a proximal sensor link of the adapter assembly of FIG. 1, according to the present disclosure.

With reference to FIGS. 25 and 26, the proximal sensor link 450 includes a distal portion 454 defining a distal cut-out 454a, and a pair of tines 454b, 454c extending distally from distal portion 454. The proximal sensor link 450 further includes a proximal portion 456 having a proximal cut-out 456a and a ring 457 disposed at a proximal end of the proximal sensor link 450. The ring 457 defines an opening 457a and includes a rib 457b disposed on an outer surface thereof for engagement with the lock spring 440 as described in further detail below.

With reference to FIGS. 27 and 29, lock mechanism 400 also includes a seal spacer 430 for aligning the load link 402 and proximal sensor link 450 within the inner housing tubes 206a, 206b. The seal spacer 430 includes four separation walls 430a-430d, which are used to separate the load link 402, proximal sensor link 450, the driver bar 258, and rotation transmitting bars 268, 270 into four quadrants, allowing for longitudinal movement thereof. The walls 430a-430d also space apart the load link 402 and the sensor link assembly 451 from the inner housing tubes 206a, 206b.

In embodiments, the seal spacer 430 may be formed from any suitable material including, but not limited to, polymers, metals, and combinations thereof. The seal spacer 430 may be formed using any suitable manufacturing methods depending on the materials being used, including but not limited to, injection molding, casting, stamping, and combinations thereof.

The seal spacer 430 may be formed within the adapter assembly 200 by injecting a liquid composition that later solidifies and forms the seal spacer 430. In embodiments, liquid siloxane polymers, such as polydimethylsiloxane, may be used. In further embodiments, two-part epoxy compositions may also be injected. In additional embodiments, the seal spacer 430 may be formed as a skeletal structure that is then contacted with a composition that reacts with the structure to form a solid structure (e.g., filling the voids). In further embodiments, the seal spacer 430 may be a foam or a sponge that is compressed prior to insertion into the adapter assembly 200 and is then allowed to expand to its original shape to fill the space of the adapter assembly 200. Expansion of the sponge/foam may be facilitated by contacting via a catalyst.

As shown in FIG. 29 the proximal portion 406 of the load link 402 is disposed between the separation walls 430a, 430b and the proximal portion 456 of the sensor link 450 is disposed between the separation walls 430a, 430d. A ring 490 secures the proximal portions 406, 450 of the load link 402 and the sensor link 450, respectively, to the seal spacer 430 while allowing for longitudinal movement thereof. The seal spacer 430 also includes an opening 431 formed therein. In embodiments, the seal spacer 430 may include a plurality of openings 431 within each quadrant. The opening 431 is used to secure the lock spring 440 therein.

Figure 28:
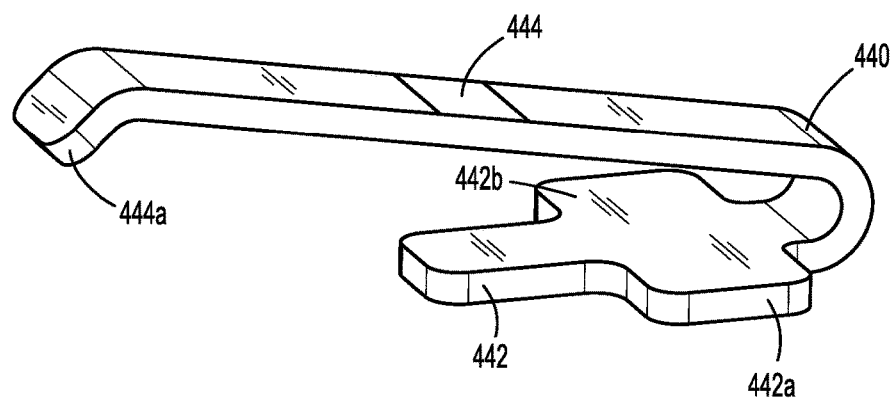
FIG. 28 is a perspective view of a lock spring of the adapter assembly of FIG. 1, according to the present disclosure.

With reference to FIG. 28, the lock spring 440 includes a base 442 configured and dimensioned to be secured to the seal spacer 430 and a resilient arm 444 extending from the base 442. In particular, the base 442 includes a pair of tabs 442a and 442b configured and dimensioned to frictionally engage a pair of opposing tabs 431a, 431b defined within the opening 431 as shown in FIG. 26. The resilient arm 444 includes an angled tab 444a configured to engage the rib 457b of the ring 457 of sensor link 450 and secure the proximal sensor link 450 as described in further detail below.

FIG. 29 shows a proximal portion of the lock mechanism 400, which includes a sensor 487 (e.g., leaf spring sensor) disposed at the distal end of the coupling cuff 254 and in longitudinal travel path of the ring 457 of the proximal sensor link 450. The sensor 487 is toggled by the proximal sensor link 450 (e.g., the ring 457) as the end effector 300 is inserted into the adapter assembly 200 as described in further detail below.

Figure 30:
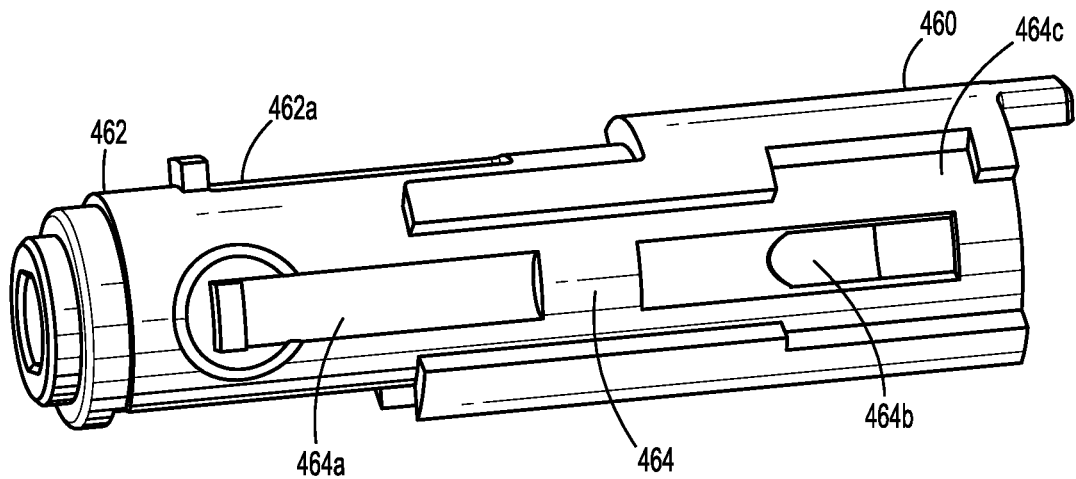
FIG. 30 is a perspective view of a distal tip housing of the adapter assembly of FIG. 1, according to the present disclosure.

With reference to FIGS. 22 and 30, the lock mechanism 400 includes a distal tip housing 460 having a first longitudinal depression 462 and a second longitudinal depression 464. The depressions 462, 464 are configured and dimensioned for longitudinal travel of the load link 402 and the proximal sensor link 450, respectively. The depression 462 also includes a channel or a groove 462a formed therein for accommodating a biasing member 470, which is also disposed within the cut-out 404a of the load link 402 as shown in FIGS. 22 and 29. The biasing member 470 pushes the load link 402 in the distal direction.

Figure 31:
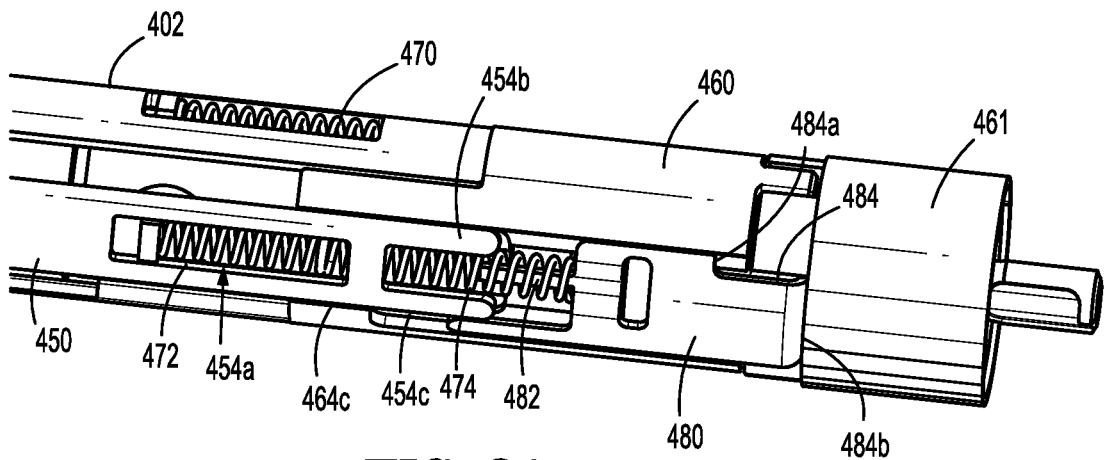
FIG. 31 is an enlarged, perspective, partially-disassembled view of a distal portion of the adapter assembly of FIG. 1 in the unloaded configuration, according to the present disclosure.
Figure 32:
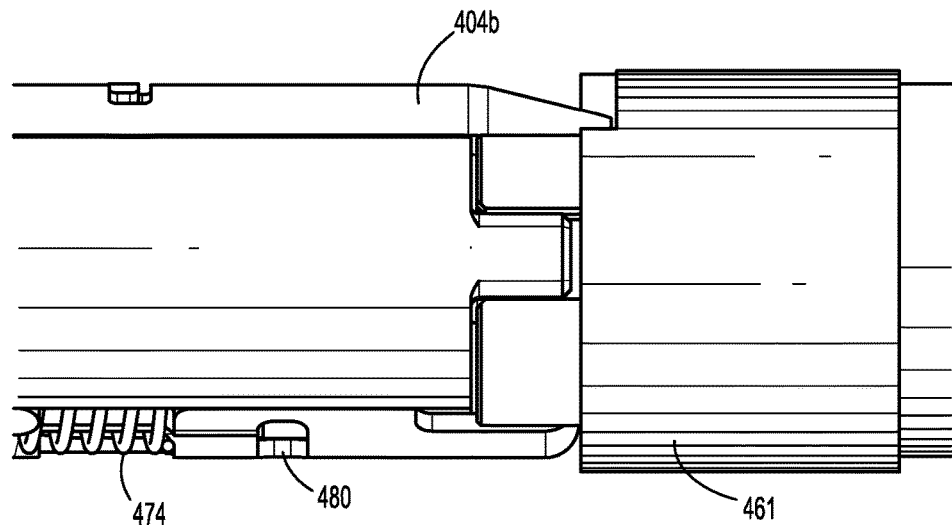
FIG. 32 an enlarged, side, partially-disassembled view of a distal portion of the adapter assembly of FIG. 1 in the unloaded configuration, according to the present disclosure.

The second longitudinal depression 464 includes a first channel 464a and a second channel 464b disposed proximally of the first channel 464a. The first channel 464a is configured and dimensioned to accommodate a biasing member 472, which is also disposed within the first channel 464a thereby pushing the proximal sensor link 450 in the distal direction as shown in FIGS. 26, 30 and 31. The second channel 464b is configured and dimensioned to accommodate a biasing member 474, which is disposed between the tines 454b, 454c of proximal sensor link 450. The depression 464 also includes a slot 464c for a distal sensor link 480. In embodiments, the biasing members 470, 472, 474 may have a substantially similar spring rate. In further embodiments, the biasing members 470, 472, 474 may have any suitable spring rate for balancing the load link 402, and the proximal and distal sensor links 450 and 480, respectively.

Figure 33:
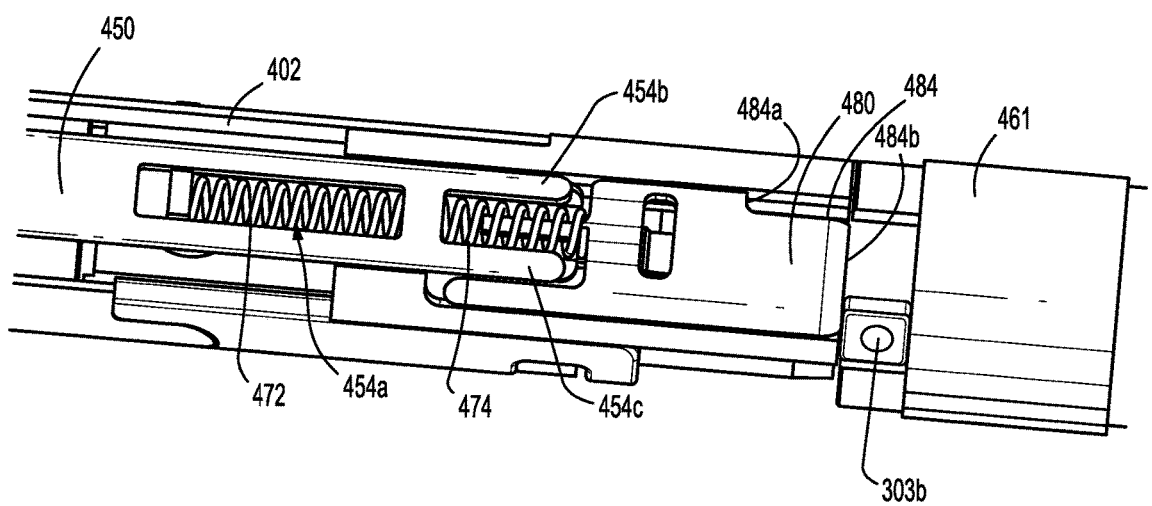
FIG. 33 is an enlarged, perspective, partially-disassembled view of the distal portion of the adapter assembly of FIG. 1 with the end effector linearly inserted therein, according to the present disclosure.

With reference to FIGS. 31 and 33, the biasing member 474 is coupled to a distal sensor link 480, with the biasing member 474 decoupling the proximal sensor link 450 from the distal sensor link 480. The distal sensor link 480 includes a proximally-facing shaft 482 configured and dimensioned to engage a distal end of the biasing member 474. The distal sensor link 480 also includes a distal edge 484 defining a stop edge 484a for interfacing with a distal portion of the slot 464c of depression 464 and a linear surface 484b for interfacing with the lug 303b of the end effector 300.

Figure 34:
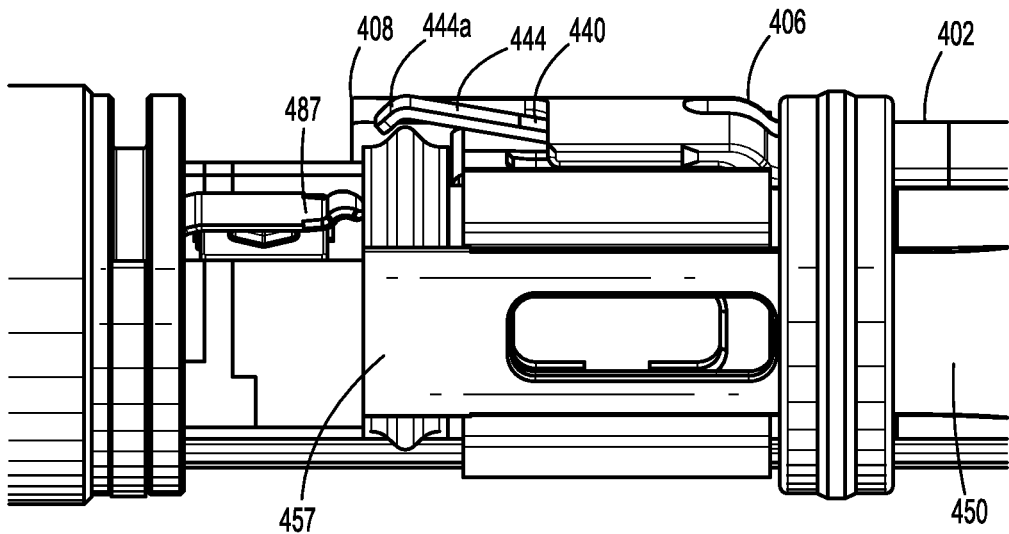
FIG. 34 is an enlarged, perspective, partially-disassembled view of a proximal portion of the adapter assembly of FIG. 1 in an unloaded configuration, according to the present disclosure.

With reference to FIGS. 29, 31, and 34, the lock mechanism 400 is illustrated in its "home" (e.g., unloaded) configuration in which the end effector 300 is not connected to the adapter assembly 200. In this configuration, the load link 402 including the finger 404b and the proximal sensor link 450 are biased (e.g., spring-loaded) distally via the biasing members 470, 472, respectively (FIG. 31). The biasing members 472 and 474 push apart the proximal and distal sensor links 450 and 480. Since the load link 402 is biased distally, the button link 408 and the ring 457 are also disposed distally, such that the button 282 and the sensor 287 are not actuated.

Figure 35:
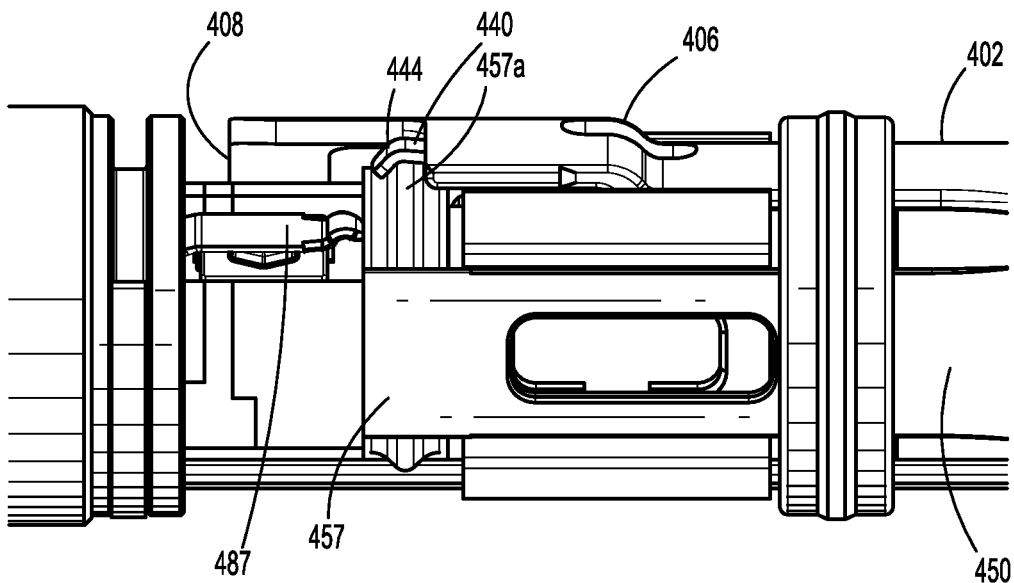
FIG. 35 is an enlarged, perspective, partially-disassembled view of the proximal portion of the adapter assembly of FIG. 1 with the end effector linearly inserted therein, according to the present disclosure.

With reference to FIGS. 33 and 35, insertion of the end effector 300 into adapter assembly 200 is illustrated. The end effector 300 is initially inserted linearly. As the end effector 300 is inserted into the bayonet connection mount 461 of the tip housing 460, the lug 303a of end effector 300 engages the finger 404b of the load link 402 pushing it proximally. In response to proximal movement of the load link 402, the proximal portion 406 of the load link 402 engages the lock spring 440 flexing down the resilient arm 444. In response thereto, the lock spring 440 engages the rib 457b of the ring 457, via the tab 444a, and secures the proximal sensor link 450. The proximal sensor link 450 remains in place as the distal sensor link 480 is engaged by the lug 303b of end effector 300 upon rotation of the end effector 300 as described in further detail below.

The lug 303b also engaged the surface 484b thereby pushing the distal sensor link 480 in the proximal direction until the distal sensor link 480 is fully moved proximally. This compresses the biasing member 474 disposed between the proximal and distal sensor links 450, 480 more so than the biasing member 472. Since the proximal sensor link 450 is immobilized by the lock spring 440, the biasing member 474 is compressed solely by the proximal sensor link 450 and biases the proximal sensor link 450 in the distal direction. In particular, the biasing member 474 is compressed more than the biasing member 472, resulting net distal biasing of the proximal sensor link 450. In embodiments, the biasing member 474 is stronger (e.g., higher spring rate) than the biasing member 472 allowing compression of the biasing member 474 to also compress the biasing member 472. However, since the ring 457 is engaged by the lock spring 440, the proximal sensor link 450 does not move distally.

Figure 36:
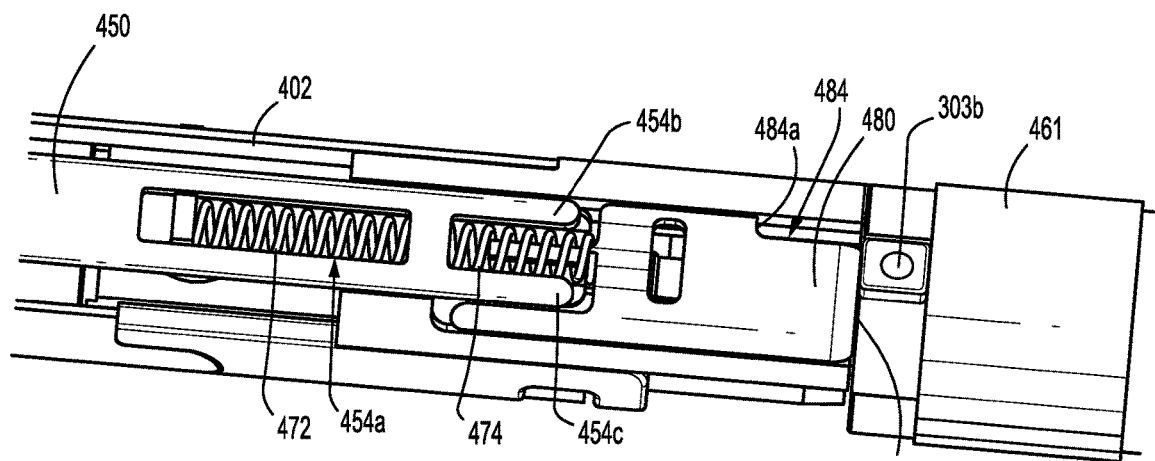
FIG. 36 is an enlarged, perspective, partially-disassembled view of the distal portion of the adapter assembly of FIG. 1 with the end effector rotated therein, according to the present disclosure.

With reference to FIG. 36, after the end effector 300 is inserted linearly, the end effector 300 is rotated about its longitudinal axis to secure the end effector 300 to the adapter 200 within the bayonet connection mount 461. Rotation of the end effector 300 causes the lugs 303a, 303b to rotate within the bayonet connection mount 461, which in turn, engages the lug 303b with the distal sensor link 480. As the lug 303b is rotated, it maintains contact with the surface 484b of distal sensor link 480 thereby maintaining the distal sensor link 480 in the proximal position.

Figure 37:
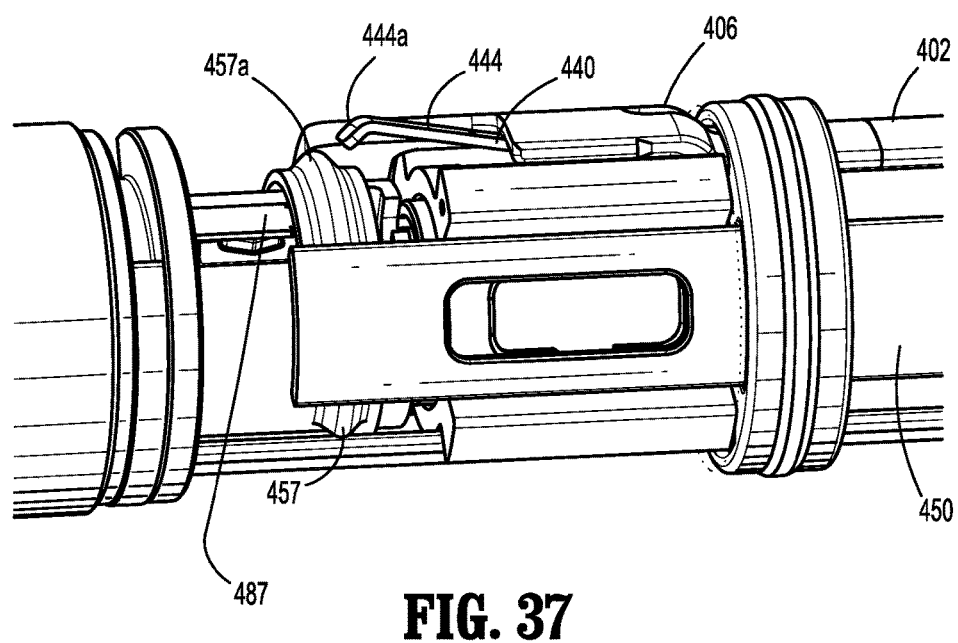
FIG. 37 is an enlarged, perspective, partially-disassembled view of the proximal portion of the adapter assembly of FIG. 1 with the end effector rotated therein, according to the present disclosure.
Figure 38:
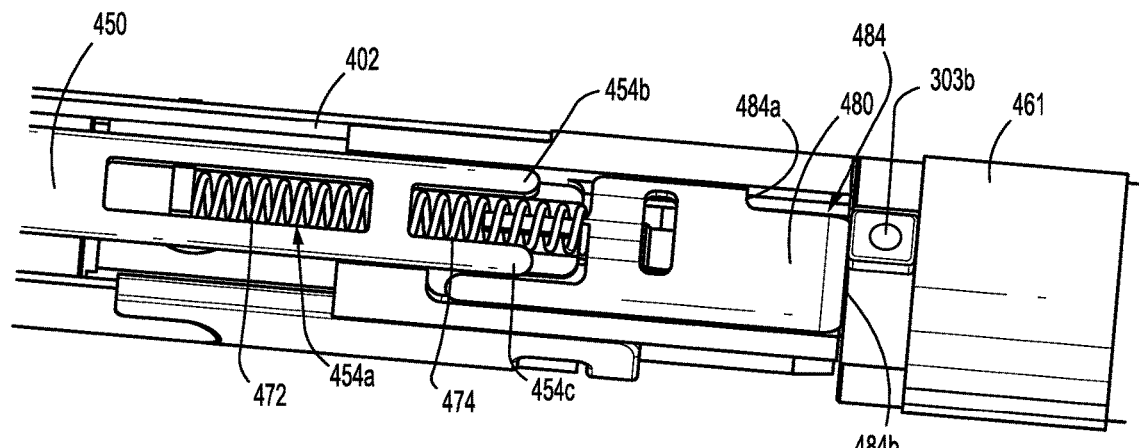
FIG. 38 is an enlarged, perspective, partially-disassembled view of the distal portion of the adapter assembly of FIG. 1 with the end effector in a locked configuration, according to the present disclosure.

With reference to FIGS. 37 and 38, once the end effector 300 is fully rotated, the lugs 303a, 303b are rotated past the finger 404b of the load link 402 and distal sensor link 480, allowing the load link 402 to move distally thereby securing the end effector 300 within the adapter 200. As the load link 402 is moved distally, the proximal portion 406 thereof is moved off the lock spring 440 thereby disengaging the rib 457a of the ring 457. This also disengages the proximal sensor link 450, which is being pushed in the proximal direction by the biasing member 474 that was being compressed between the proximal and distal sensor links 450 and 480. In particular, the biasing member 474 is under more compression than the biasing member 472.

As shown in FIG. 38, as the distal sensor link 480 is maintained in the proximal position by the lug 303b of end effector 300. The proximal sensor link 450 is then moved proximally due to the equalization of the compression of the biasing members 472 and 474 as the ring 457 is released. The proximal sensor link 450, namely, the ring 457, comes in contact with and toggles the sensor 487. This signals the surgical instrument 100 that the end effector 300 has been inserted and secured.

Figure 39:
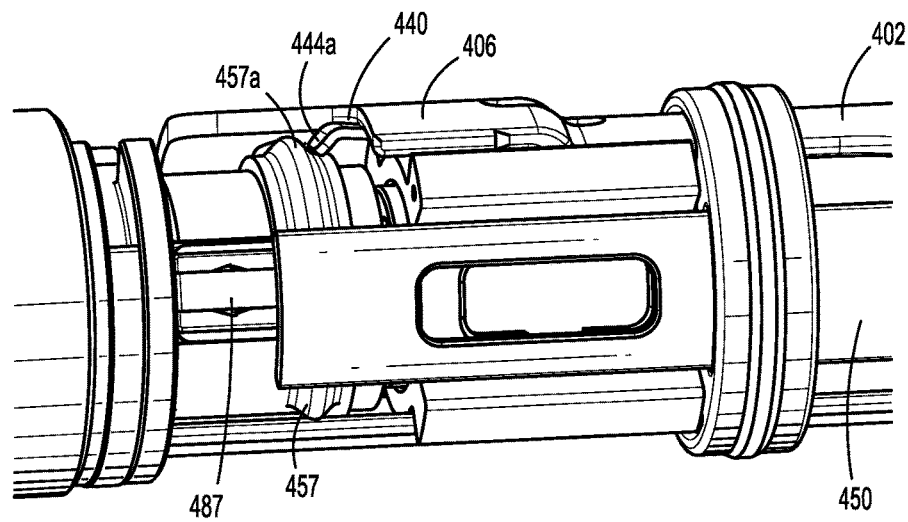
FIG. 39 is an enlarged, perspective, partially-disassembled view of the proximal portion of the adapter assembly of FIG. 1 with the end effector in an unlocked configuration, according to the present disclosure.

With reference to FIG. 39, disconnection of the end effector 300 is described. Once the end effector 300 has been loaded, actuation of the button 282 moves the load link 402 in a proximal direction, which allows for rotation of the end effector 300 and its removal from the adapter 200. This moves the load link 402 in the proximal direction without signaling the surgical instrument 100 that the end effector 300 has been disengaged since the proximal sensor link 450 remains seated on the sensor 487. While the release button 282 (e.g., the load link 402) is continuously engaged in the proximal direction, the end effector 300 is rotated and then pulled out from the adapter assembly 200. Rotational movement of the end effector 300 moves the lug 303b of end effector 300 from the distal sensor link 480, allowing the distal sensor link 480 to move distally due to the biasing member 474. This in turn, allows the proximal sensor link 450 to also move in the distal direction and release the sensor 487, thereby toggling the sensor 487 to signal the surgical instrument 100 that the end effector 300 has been removed.

In embodiments, the load link 402 and the proximal sensor link 450 and other components of the lock mechanism 400 may be formed from any suitable material including, but not limited to, polymers, metals, and combinations thereof. The components may be formed using any suitable manufacturing methods depending on the materials being used, including but not limited to, injection molding, casting, stamping, and combinations thereof. The components may be formed as integral pieces or formed from two or more subcomponents (e.g., ring 457 being coupled to proximal sensor link 450) that are then assembled. The subcomponents may be coupled using any suitable techniques including, but not limited to, adhesives (e.g., epoxy), soldering, welding, friction fitting, snap fitting, and combinations thereof.

Figure 40:
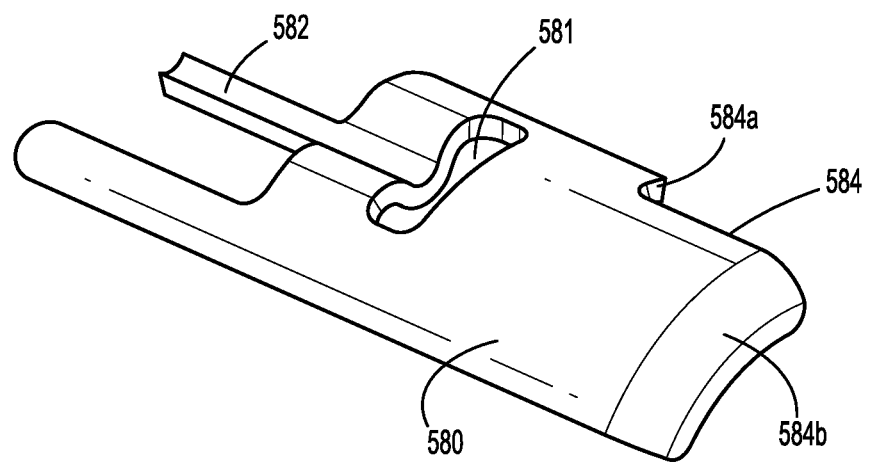
FIG. 40 is a perspective view of a distal sensor link of the adapter assembly of FIG. 1, according to the present disclosure.
Figure 41:
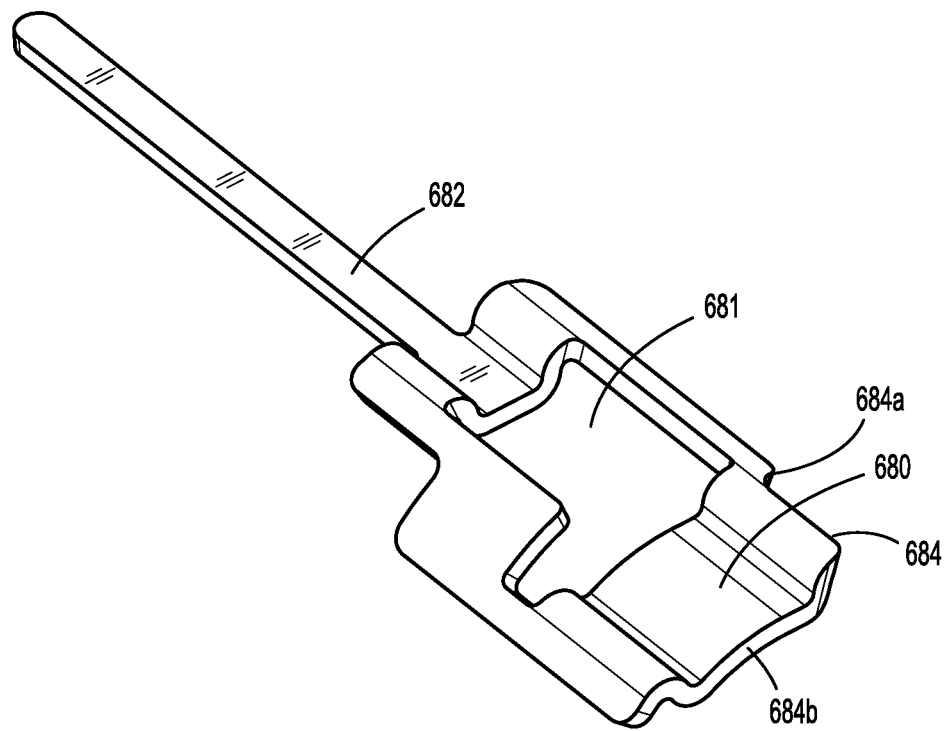
FIG. 41 is a perspective view of a distal sensor link of the adapter assembly of FIG. 1, according to another embodiment of the present disclosure.
Figure 42:
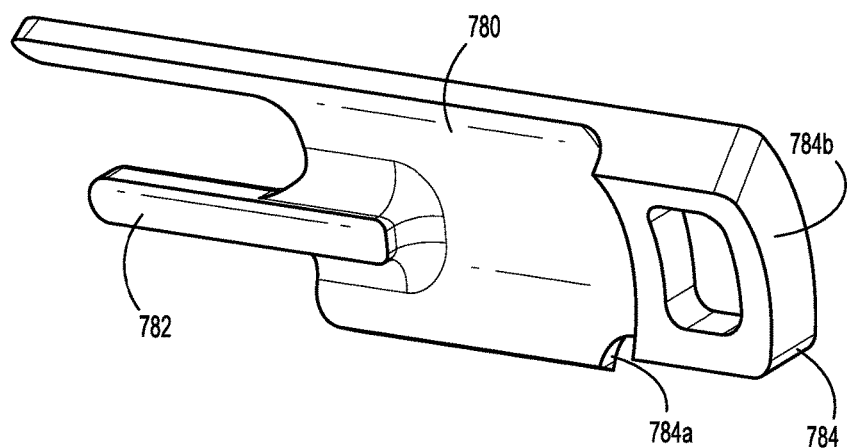
FIG. 42 is a perspective view of a distal sensor link of the adapter assembly of FIG. 1, according to a further embodiment of the present disclosure.

FIGS. 40-42 show various embodiments of distal sensor links 580, 680, 780, which are substantially similar to the distal sensor link 480 of FIG. 31 and only the differences between the distal sensor links 480, 580, 680, and 780 are described.

With reference to FIGS. 40 and 41 the distal sensor links 580 and 680 are formed from sheet metal or any other suitable malleable material. In embodiments, the distal sensor links 580 and 680 may be formed by stamping. The distal sensor link 780 may be formed by injection molding from polymers, metals, combinations thereof, and the like. Each of the distal sensor links 580, 680, 780 includes a proximally-facing shaft 582, 682, 782, respectively configured and dimensioned to engage a distal end of the biasing member 474. Each of the distal sensor links 580, 680, 780 also includes a distal edge 584, 684, 784 defining a stop edge 584a, 684a, 784a for interfacing with a distal portion of the slot 464c (FIG. 30) and a linear surface 584b, 684b, 784b for interfacing with the lug 303b of the end effector 300. Each of the distal sensor links 580 and 680 also includes an opening therein 581, 681, which acts as a stress-relief feature allowing for three-dimensional shaping of the distal sensor links 580 and 680 during stamping.

With reference to FIGS. 43-55, another embodiment of a lock mechanism 500 is shown. The lock mechanism 500 is substantially similar to the lock mechanism 400 of FIGS. 22-39 and only the differences therebetween are described.

Lock mechanism 500 includes a load link 502 that extends longitudinally through outer tube 206. The lock mechanism 500 also includes a sensor link assembly 551 having a proximal sensor link 550. The link assembly 551 includes any suitable distal sensor link 480.

With reference to FIGS. 43-46, load link 502 includes a distal portion 504, which is substantially similar to the distal portion 404 of the load link 402. The load link 502 further includes a proximal portion 506 having a pair of tines 509a, 509b defining an opening 507, which is configured and dimensioned to engage a button link 508. The button link 508 is configured and dimensioned to engage the button 282 and the lock spring 440 as described in further detail below.

The button link 508 includes a mounting portion 511 having a pair of guides 511a, 511b (e.g., folds) configured to frictionally engage the pair of tines 509a, 509b, respectively. The mounting portion 511 also includes a cutout 511c having a contact edge 511d for contacting the lock spring 440. A button shaft 513 extends from the mounting portion 511 and is configured to engage the button 282.

Figure 47:
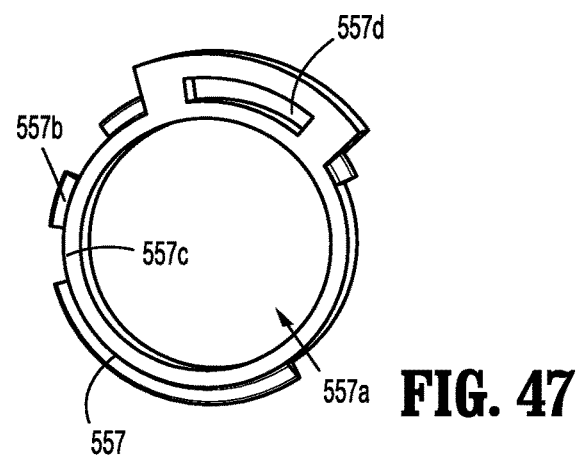
FIG. 47 is a front view of a ring of the adapter assembly of FIG. 43, according to another embodiment of the present disclosure.
Figure 48:
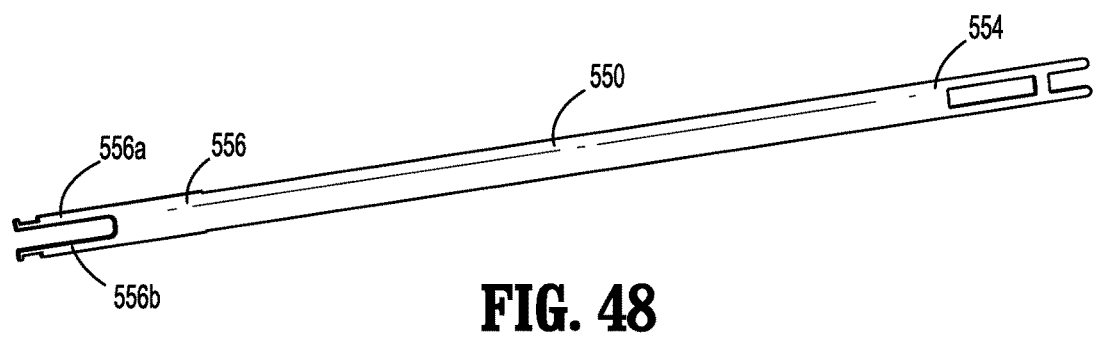
FIG. 48 is a perspective view of a proximal sensor link of the adapter assembly of FIG. 43, according to the present disclosure.
Figure 49:
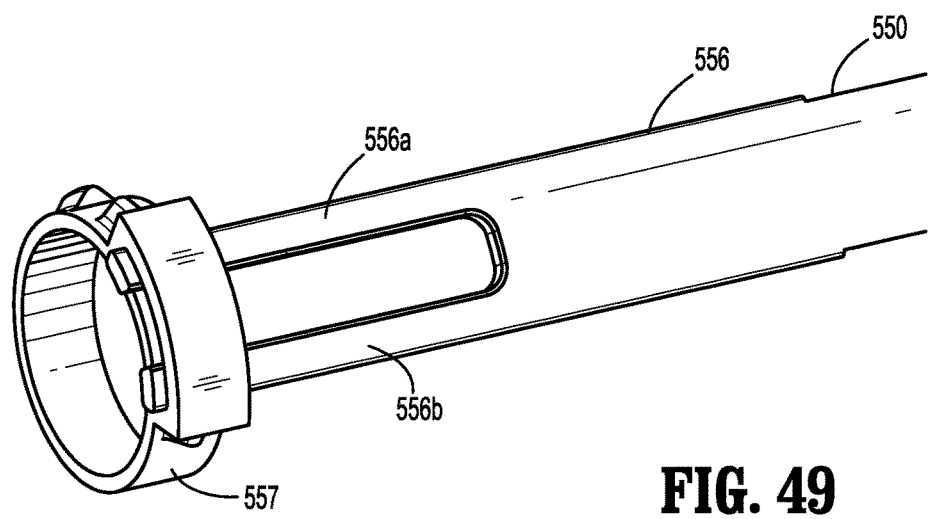
FIG. 49 is a perspective view of a proximal portion of the proximal sensor link of FIG. 48, according to the present disclosure.
Figure 50:
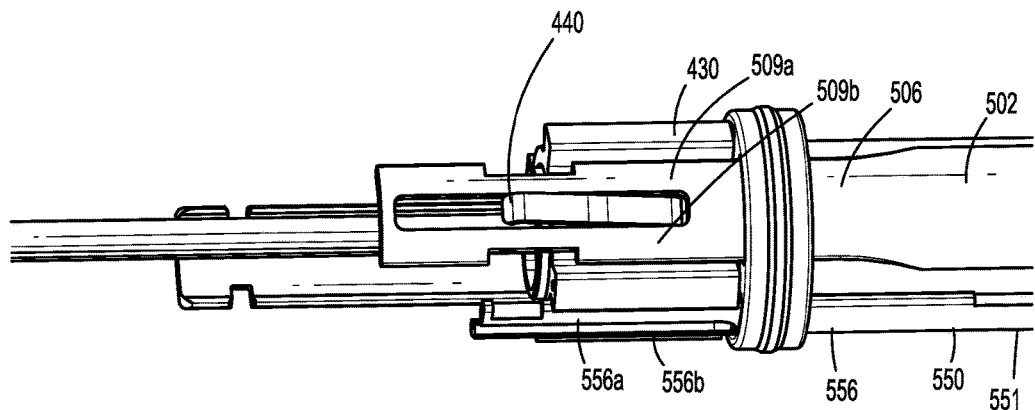
FIGS. 50-55 are an enlarged, perspective, partially-disassembled view of the proximal portion of an adapter assembly of FIG. 42 illustrating assembly thereof, according to the present disclosure.

With reference to FIGS. 47-49, the proximal sensor link 550 includes a distal portion 554, which is substantially similar to the distal portion 454 of the load link 450. The proximal sensor link 550 further includes a proximal portion 556 having a pair of flexible tabs 556a, 556b configured to engage a ring 557.

The ring 557 defines an opening 557a and includes a depression 556c for accommodating the proximal portion 506 of the load link 502. The ring 557 also includes a nub 557b disposed on an outer surface of the depression 556c for engagement with the lock spring 440 as described in further detail below. The ring 557 includes a slot 557d for engaging the flexible tabs 556a, 556b of the proximal sensor link 550.

Figure 43:
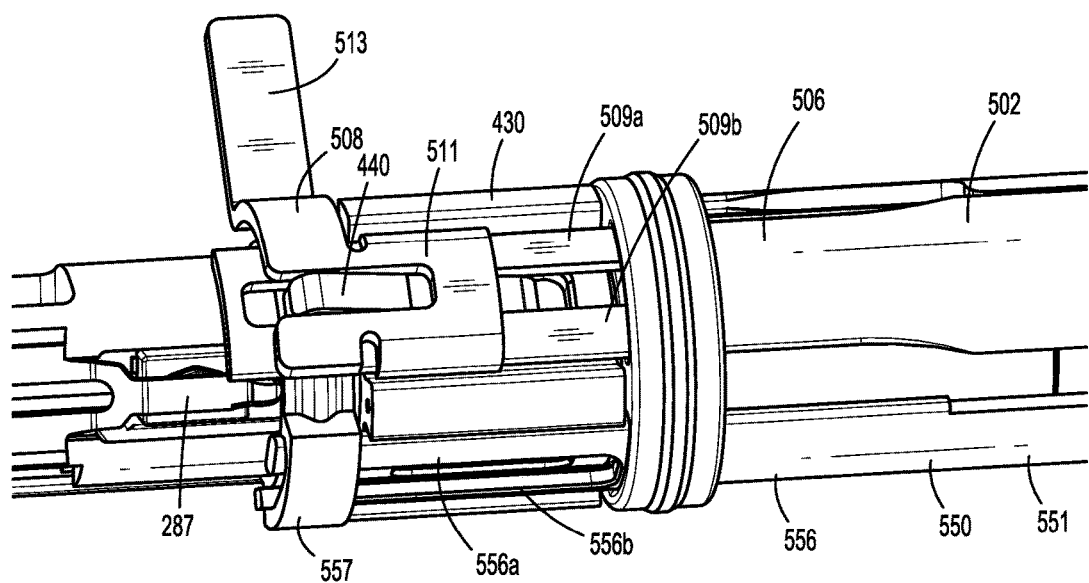
FIG. 43 is an enlarged, perspective, partially-disassembled view of the proximal portion of an adapter assembly according to another embodiment of the present disclosure.
Figure 44:
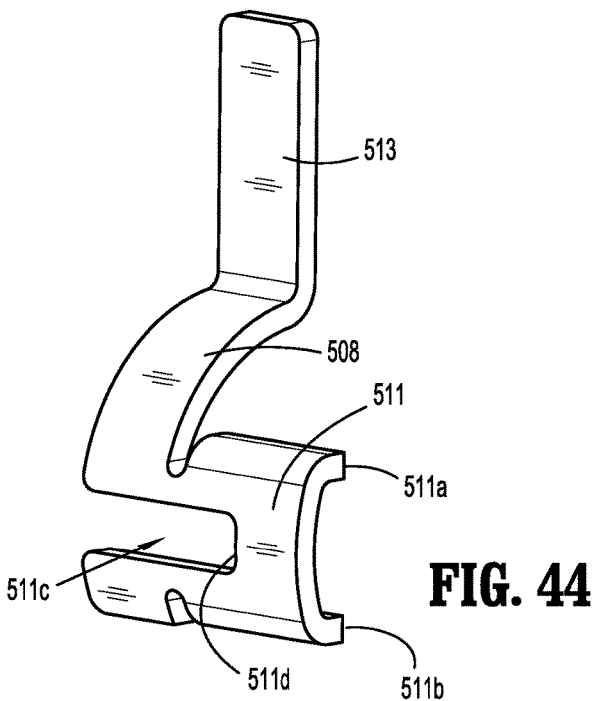
FIG. 44 is a perspective view of a button link of the adapter assembly of FIG. 43, according to the present disclosure.
Figure 45:
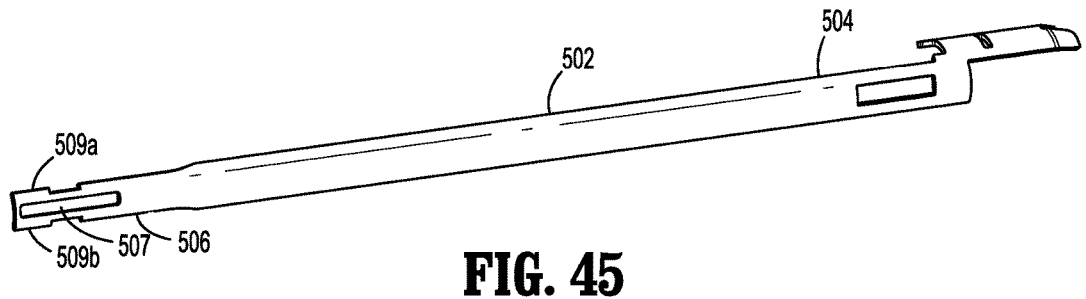
FIG. 45 is a perspective view of a load link of the adapter assembly of FIG. 43, according to the present disclosure.
Figure 46:
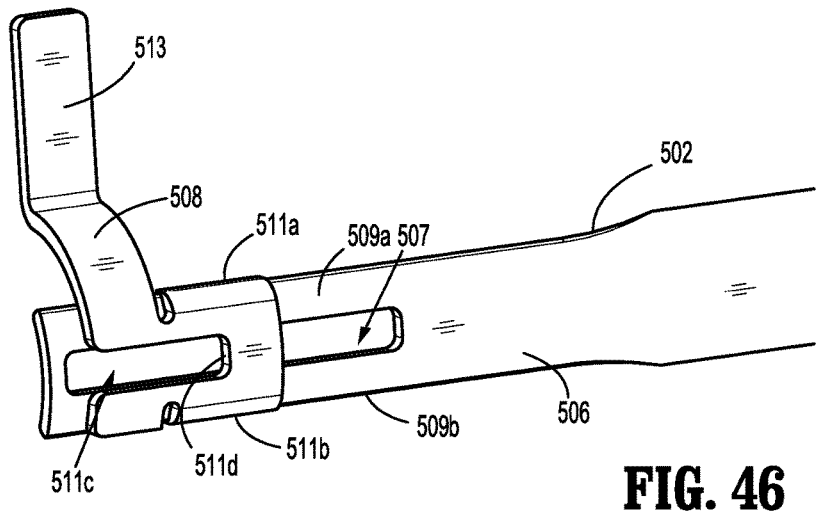
FIG. 46 is a perspective view of a proximal portion of the load link of FIG. 45, according to the present disclosure.
Figure 51:
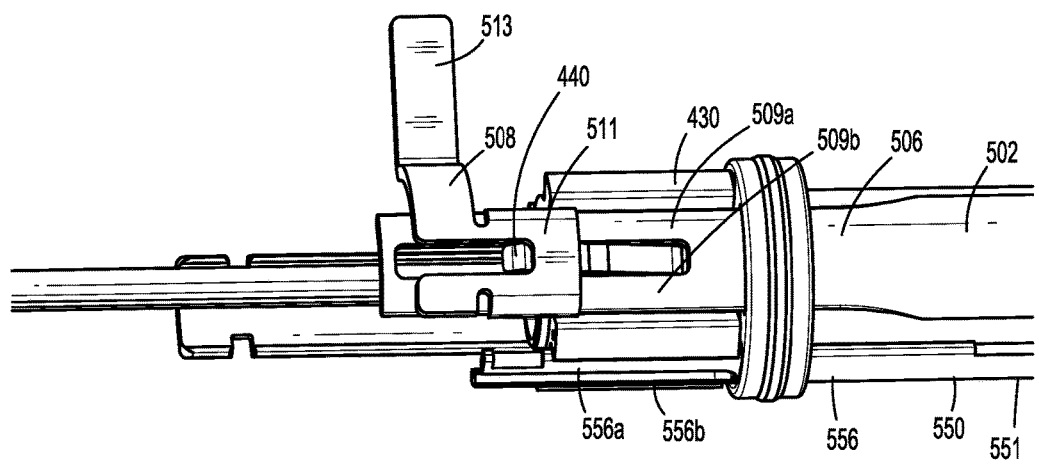
Figure 52:
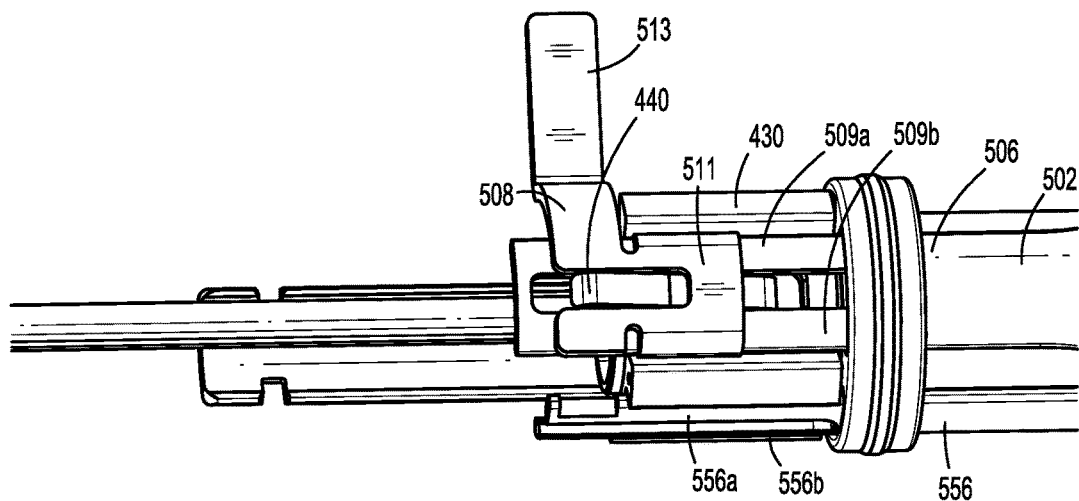
Figure 53:
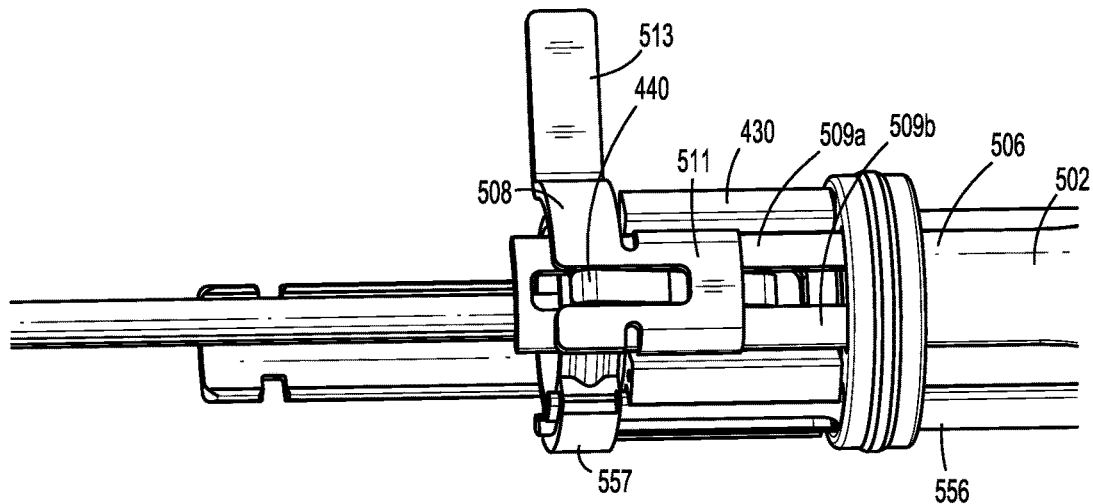
Figure 54:
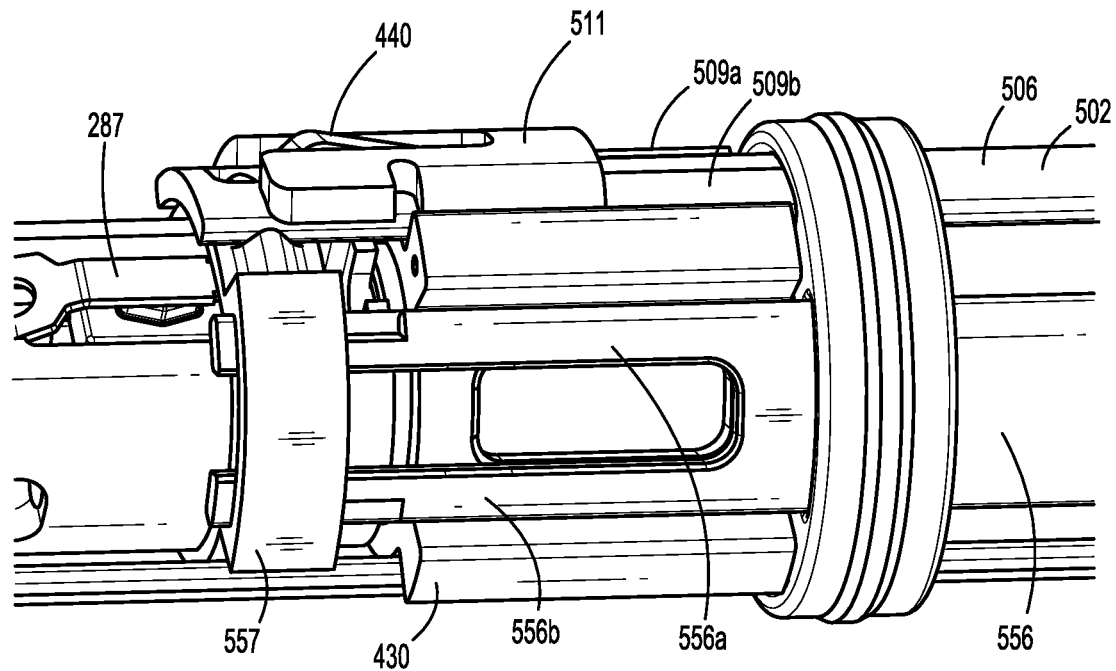
Figure 55:
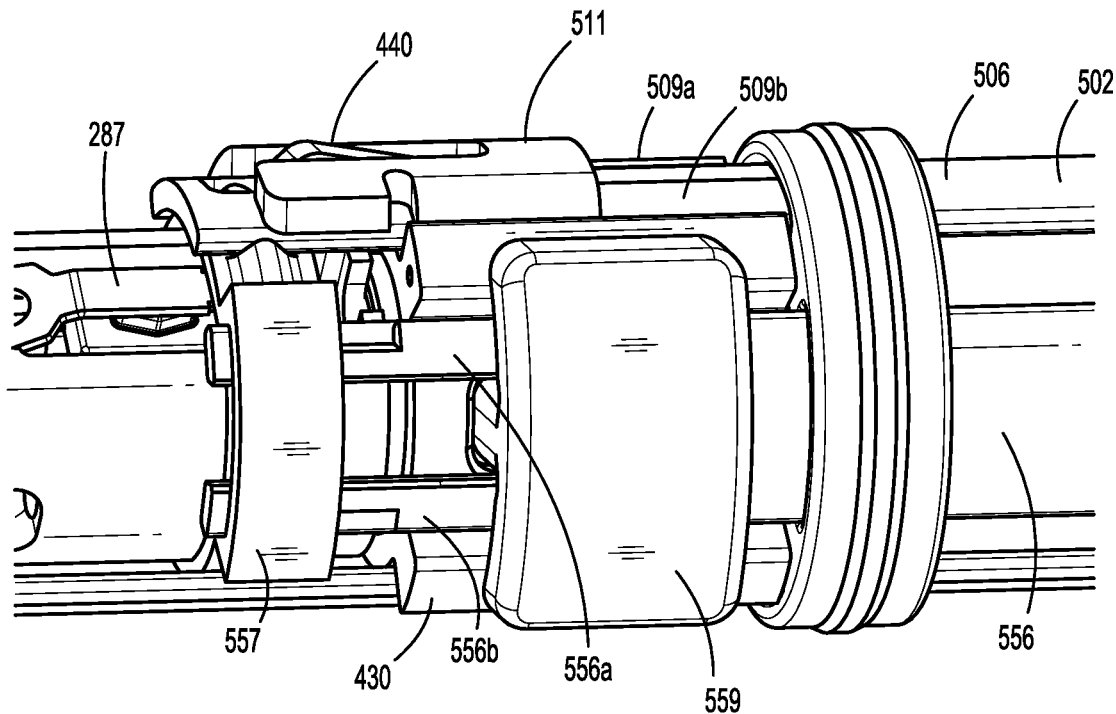

With reference to FIG. 43, the lock mechanism 500 also includes the seal spacer 430 for aligning the load link 502 and proximal sensor link 550 within the inner housing tubes 206a, 206b. FIGS. 50-55 show assembly of the lock mechanism 500. Initially, the seal spacer 430 is inserted between the load link 502 and proximal sensor link 550 as described above. Thereafter, the button link 508 is coupled to the proximal portion 502 of the load link 502 as shown in FIG. 51. The load link 502 is pulled proximally to aid in the assembly. With reference to FIG. 52, the load link 502 is pushed distally into its home position to disengage the lock spring 440. With reference to FIG. 53, the ring 557 is coupled to the proximal portion 556 of the proximal sensor link 550. The lock mechanism 500 is thereafter coupled to the proximal portion of the adapter assembly 200 including the sensor 287 as shown in FIG. 54. With reference to FIG. 55, an anchor 559 is coupled to the seal spacer 430 to secure the proximal portion 556 of the proximal sensor link 550 to the seal spacer 430 between the flexible tabs 556a, 556b.

Figure 56A:
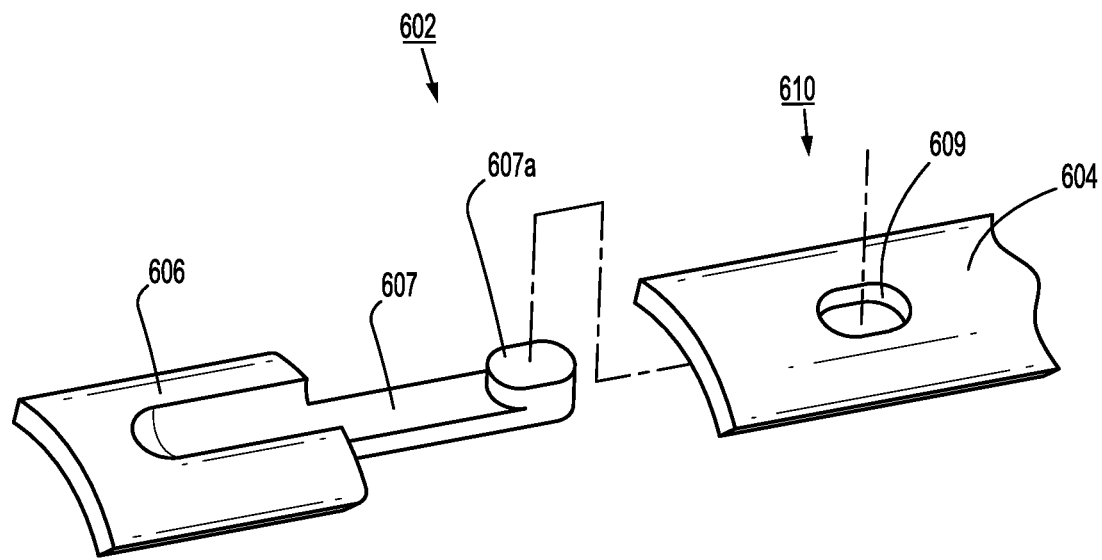
FIGS. 56A-C are perspective, schematic views of a multi-part load link, according to the present disclosure.
Figure 56B:
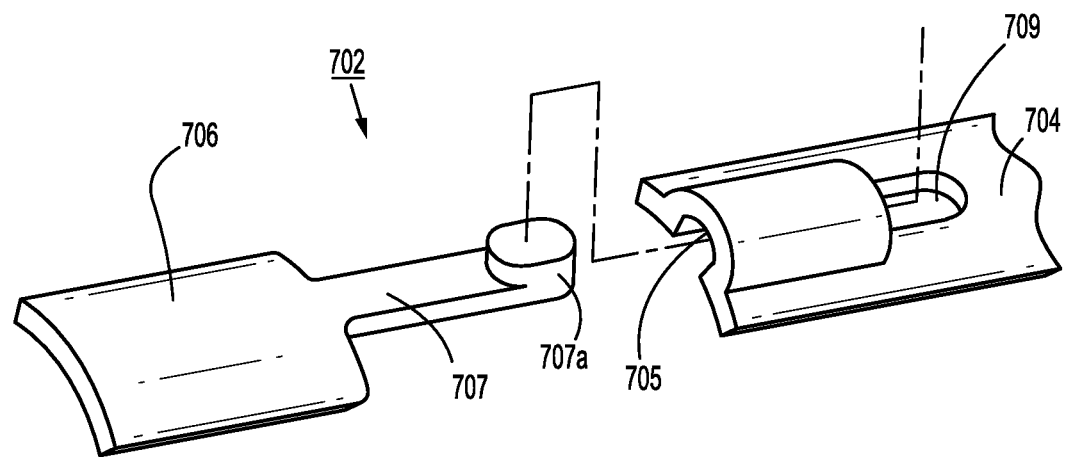
Figure 56C:
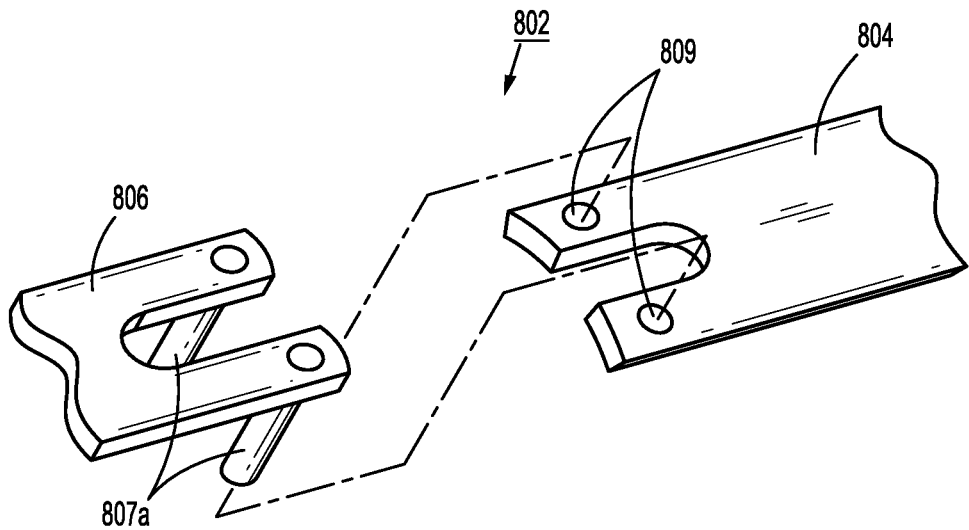

FIGS. 56A-C show various embodiments of multi-part load links 602, 702, 802. The load links 602, 702, 802 are substantially similar to the load link 402 of FIGS. 23 and 24 and only the differences therebetween are described. With reference to FIG. 56A, the load link 602 includes a proximal portion 606 and a distal portion 604 that are interconnected via a locking tab assembly 610. The distal portion 604 includes an opening 609. The proximal portion 606 includes a resilient tab 607 having a protrusion 607a at a distal end thereof configured and dimensioned to fit within the opening 609. During assembly, the distal and proximal portions 604, 606 are pushed together, with the resilient tab 607 being deflected until the protrusion 607a is within the opening 609, at which point the resilient tab 607 maintains the protrusion 607a therein.

With reference to FIG. 56B, the load link 702 is substantially similar to the load link 602. The load link 702 includes a distal portion 704 having a longitudinal groove 705 and an opening 709. The load link 702 also includes a proximal portion 706 that includes a resilient tab 707 having a protrusion 707a at a distal end thereof configured and dimensioned to fit within the opening 709. The groove 705 is configured and dimensioned to guide the protrusion 707a to the opening 709.

With reference to FIG. 56C, the load link 802 includes a distal portion 804 having a pair of openings 809 and a proximal portion 806 having a pair of tabs 807. Each of the tabs 807 includes a post 807a configured and dimensioned to frictionally engage the openings 809, thus obviating the need for resilient tabs.

Figure 57:
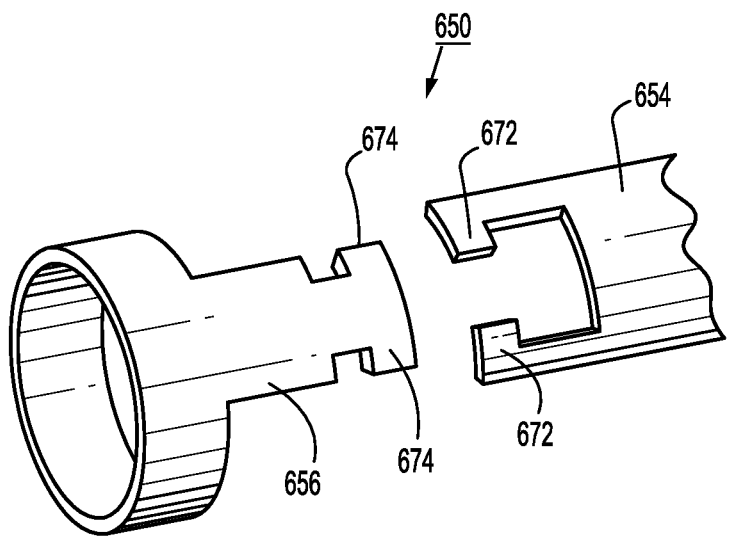
FIG. 57 is a perspective, schematic view of a multi-part proximal sensor link, according to the present disclosure.

FIG. 57 shows a multi-part proximal sensor link 650. The proximal sensor link 650 is substantially similar to the proximal sensor link 450 of FIGS. 25 and 26 and only the differences therebetween are described. The proximal sensor link 650 includes a distal portion 654 having diametrically opposed inwardly extending fingers 672. The proximal sensor link 650 also includes a proximal portion 656 having opposed outwardly extending tabs 674. During assembly, the distal and proximal portions 654, 656 are pushed together with the fingers 672 engaging the tabs 674.

Figure 58:
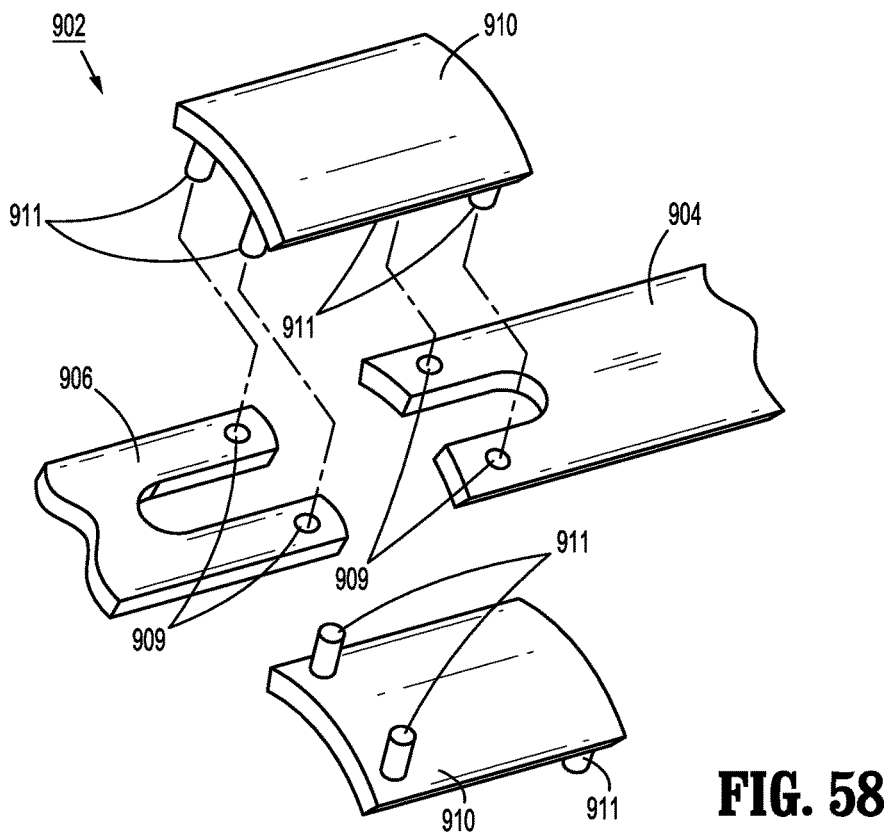
FIG. 58 is a perspective, schematic view of a multi-part load link, according to another embodiment of the present disclosure.

FIG. 58 shows another embodiment of a multi-part load link 902, which is substantially similar to the load link 402 of FIGS. 23 and 24 and only the differences therebetween are described. The load link 902 includes a proximal portion 906 and a distal portion 904 that are interconnected via a connector plate 910. Each of the distal portion 904 and the proximal portion 906 includes one or more openings 909. The connector plate 910 includes one or more posts 911 at proximal and distal ends thereof configured and dimensioned to frictionally fit within the openings 909. In embodiments, the posts 911 may be disposed on either the top and/or bottom surfaces of the connector plate 910. During assembly, the connector plate 910 is coupled to both the distal and proximal portions 904, 906 to secure the distal and proximal portions 904, 906.

Figure 59:
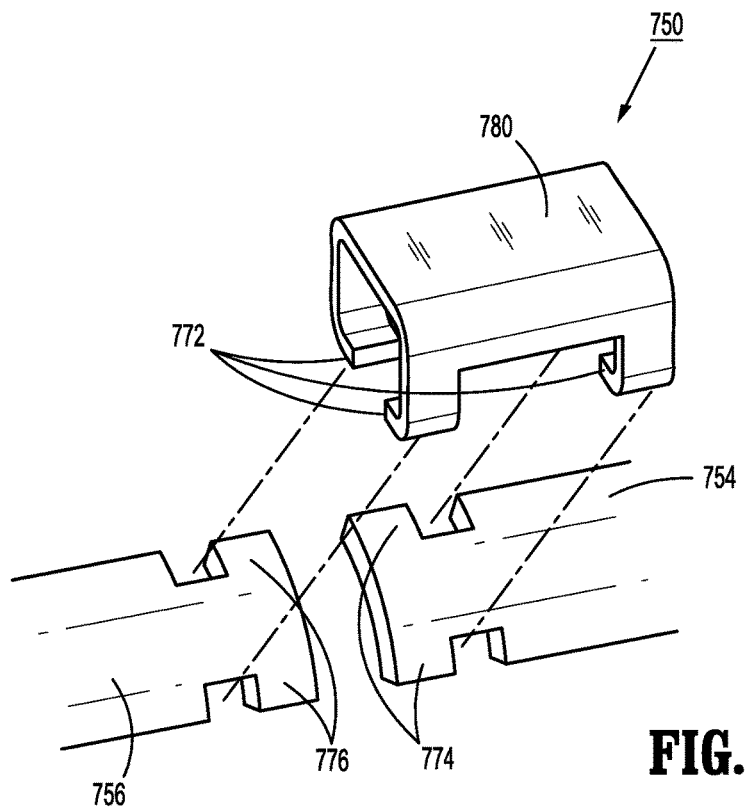
FIG. 59 is a perspective, schematic view of a multi-part proximal sensor link, according to another embodiment of the present disclosure.

FIG. 59 shows a multi-part proximal sensor link 750. The proximal sensor link 750 is substantially similar to the proximal sensor link 450 of FIGS. 25 and 26 and only the differences therebetween are described. The proximal sensor link 750 includes a distal portion 754 and a proximal portion 756, each of which includes outwardly extending tabs 774 and 776, respectively. The proximal sensor link 750 also includes a connector plate 780 having diametrically opposed inwardly extending fingers 772 at its proximal and distal ends. During assembly, the connector plate 780 is coupled to both the distal and proximal portions 754, 756 as the fingers 772 engage the tabs 774 and 776 to secure the distal and proximal portions 754, 756.

It will be understood that various modifications may be made to the embodiments disclosed herein. For example, the instrument 100 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as

The invention claimed is:

1. A surgical device adapter for coupling an end effector to a handle assembly, the surgical device adapter comprising:
   a sensor link assembly longitudinally movable and engagable by the end effector upon coupling the end effector to the surgical device adapter;
   a load link movable by the end effector from a first longitudinal position to a second longitudinal position, wherein in the second longitudinal position the load link locks the sensor link assembly and in the first longitudinal position releases the sensor link assembly; and
   a sensor engagable by the sensor link assembly upon proximal movement thereof in response to release by the load link.

2. The surgical device adapter according to claim 1, wherein the load link is distally biased and is configured to prevent proximal movement of the sensor link assembly until the load link is distally biased and the end effector is coupled to the surgical device adapter.

3. The surgical device adapter according to claim 2, further comprising a lock spring actuatable by proximal movement of the load link, the lock spring configured to couple to a proximal portion of the sensor link assembly and prevent proximal movement thereof.

4. The surgical device adapter according to claim 3, wherein the sensor link assembly comprises a proximal sensor link, a distal sensor link and a biasing member disposed therebetween.

5. The surgical device adapter according to claim 4, wherein the proximal sensor link comprises a ring configured to interface with the lock spring.

6. The surgical device adapter according to claim 4, wherein the surgical device adapter comprises a bayonet connection at a distal end thereof configured to couple to a pair of lugs of the end effector.

7. The surgical device adapter according to claim 6, wherein the end effector is configured to be inserted linearly into the bayonet connection.

8. The surgical device adapter according to claim 7, wherein the load link is moved proximally to allow for rotation of the pair of lugs within the bayonet connection.

9. The surgical device adapter according to claim 8, wherein at least one lug of the pair of lugs engages the distal sensor link upon rotation of the end effector within the bayonet connection thereby compressing the biasing member.

10. The surgical device adapter according to claim 9, wherein the load link is moved distally to secure at least one lug of the pair of lugs within the bayonet connection.

11. The surgical device adapter according to claim 10, wherein distal movement of the load link releases the lock spring allowing the biasing member to move the proximal sensor link proximally to engage the sensor.

12. A method for coupling an end effector to a surgical device adapter, comprising the steps of:
    inserting an end effector comprising a pair of lugs disposed at a proximal end thereof into a distal end of the surgical device adapter;
    proximally moving a distally-biased load link within the surgical device adapter to secure a sensor link assembly;
    rotating the end effector within the adapter assembly, wherein at least one lug of the pair of lugs engages and secures at least a portion of the sensor link assembly; and
    distally moving the distally-biased load link to secure the end effector within the surgical device adapter and to release the sensor link assembly allowing the sensor link assembly to move proximally to engage a sensor.

13. The method according to claim 12, wherein the sensor link assembly comprises a distally-biased proximal sensor link, a distal sensor link, and a biasing member disposed therebetween.

14. The method according to claim 13, wherein moving the distally-biased load link proximally secures the distally-biased proximal sensor link.

15. The method according to claim 14, wherein rotating the end effector engages at least one lug of the pair of lugs and engages the distal sensor link thereby compressing the biasing member.

16. The method according to claim 15, moving the distally-biased load link distally secures at least one lug of the pair of lugs to release the distally-biased proximal sensor link allowing the biasing member to move the distally-biased proximal sensor link proximally to engage the sensor.

17. The method according to claim 12, wherein the distally-biased load link is coupled to the sensor link assembly via a biasing member at proximal ends thereof.

* * * * *